(12) United States Patent
Ishikawa et al.

(10) Patent No.: US 11,246,708 B2
(45) Date of Patent: Feb. 15, 2022

(54) MEDICAL USE HONEYCOMB STRUCTURE

(71) Applicant: KYUSHU UNIVERSITY, NATIONAL UNIVERSITY CORPORATION, Fukuoka (JP)

(72) Inventors: Kunio Ishikawa, Fukuoka (JP); Kanji Tsuru, Fukuoka (JP); Akira Tsuchiya, Fukuoka (JP); Yuki Sugiura, Fukuoka (JP); Yasuharu Nakashima, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 16/342,338

(22) PCT Filed: Oct. 16, 2017

(86) PCT No.: PCT/JP2017/037413
§ 371 (c)(1),
(2) Date: Apr. 16, 2019

(87) PCT Pub. No.: WO2018/074429
PCT Pub. Date: Apr. 26, 2018

(65) Prior Publication Data
US 2020/0046503 A1 Feb. 13, 2020

(30) Foreign Application Priority Data
Oct. 17, 2016 (JP) .............................. JP2016-203318

(51) Int. Cl.
*A61F 2/30* (2006.01)
*A61F 2/28* (2006.01)
(Continued)

(52) U.S. Cl.
CPC ............ *A61F 2/30767* (2013.01); *A61F 2/28* (2013.01); *A61L 27/12* (2013.01); *A61L 27/56* (2013.01);
(Continued)

(58) Field of Classification Search
CPC .......... A61F 2/28; A61F 2/30767; B32B 3/26; B28B 3/20
See application file for complete search history.

(56) References Cited

U.S. PATENT DOCUMENTS 7,147,666 B1  12/2006  Grisoni
2006/0225619 A1*  10/2006  Ishikawa ................. A61L 27/12
106/690

(Continued)

FOREIGN PATENT DOCUMENTS

CN  1767794  5/2006
EP  2607336 A1  6/2013
(Continued)

OTHER PUBLICATIONS

Nakano et al., "Unique alignment and texture of biological apatite crystallites in typical calcified tissues analyzed by microbeam X-ray diffractometer system", Bone, Oct. 2002, pp. 479-487.
(Continued)

*Primary Examiner* — Jason-Dennis N Stewart
(74) *Attorney, Agent, or Firm* — Greenblum & Bernstein, P.L.C.

(57) ABSTRACT

A medical use honeycomb structure having a plurality of through-holes extending in one direction, wherein an outer peripheral section of the medical use honeycomb structure has a through-hole groove formed by incomplete side walls of the through-hole, and a through-hole inlet adjacent to the through-hole groove.

28 Claims, 11 Drawing Sheets

(51) Int. Cl.
   *B28B 3/20*    (2006.01)
   *B28B 11/24*   (2006.01)
   *C04B 38/00*   (2006.01)
   *C04B 14/36*   (2006.01)
   *C04B 35/447*  (2006.01)
   *A61L 27/12*   (2006.01)
   *A61L 27/56*   (2006.01)

(52) U.S. Cl.
   CPC .............. *B28B 3/20* (2013.01); *B28B 11/243* (2013.01); *C04B 14/366* (2013.01); *C04B 35/447* (2013.01); *C04B 38/0006* (2013.01); *A61F 2002/30785* (2013.01); *A61F 2002/30911* (2013.01); *A61F 2002/30968* (2013.01); *A61F 2310/00221* (2013.01); *A61F 2310/00293* (2013.01); *A61L 2430/02* (2013.01); *B28B 2003/203* (2013.01); *Y10T 428/24149* (2015.01)

(56) References Cited

U.S. PATENT DOCUMENTS

| | | | |
|---|---|---|---|
| 2008/0097618 | A1 | 4/2008 | Baker et al. |
| 2008/0099948 | A1 | 5/2008 | Hakamatsuka et al. |
| 2010/0075419 | A1* | 3/2010 | Inagaki ................ A61L 27/56 |
| | | | 435/402 |
| 2010/0222883 | A1 | 9/2010 | Kimura et al. |
| 2011/0295383 | A1 | 12/2011 | Ishikawa et al. |
| 2013/0218288 | A1* | 8/2013 | Fonte .................. A61L 27/306 |
| | | | 623/23.5 |
| 2017/0252480 | A1 | 9/2017 | Ishikawa et al. |
| 2017/0258574 | A1 | 9/2017 | Hutmacher et al. |

FOREIGN PATENT DOCUMENTS

| | | |
|---|---|---|
| JP | 5-084713 A | 4/1993 |
| JP | 2003-320515 A | 11/2003 |
| JP | 2003-335574 | 11/2003 |
| JP | 3470759 B2 | 11/2003 |
| JP | 2004-298407 A | 10/2004 |
| JP | 2004-298545 A | 10/2004 |
| JP | 2005-110709 A | 4/2005 |
| JP | 2005-152006 A | 6/2005 |
| JP | 3858069 B2 | 12/2006 |
| JP | 3940770 B2 | 7/2007 |
| JP | 2008-230910 A | 10/2008 |
| JP | 2010-18459 A | 1/2010 |
| JP | 4802317 B2 | 10/2011 |
| JP | 2012-148929 A | 8/2012 |
| WO | 2004/040036 A1 | 5/2004 |
| WO | 2004/112856 A1 | 12/2004 |
| WO | 2008/041563 A1 | 4/2008 |
| WO | 2009/034876 | 3/2009 |
| WO | 2016/035751 | 3/2016 |
| WO | 2016/038083 | 3/2016 |

OTHER PUBLICATIONS

Ishimoto et al., "Degree of biological apatite c-axis orientation rather than bone mineral density controls mechanical function in bone regenerated using recombinant bone morphogenetic protein-2", Journal of Bone and Mineral Research, May 2013, pp. 1170-1179.
Nakano et al., "Biological apatite (BAp) crystallographic orientation and texture as a new index for assessing the microstructure and function of bone regenerated by tissue engineering", Bone, Jul. 2012, pp. 741-747.
International Search Report received in PCT/JP2017/037413, dated Dec. 12, 2017.
Xiang Li et al., "Fabrication and compressive properties of Ti6A14V implant with honeycomb-like structure for biomedical applications", Rapid Prototyping Journal, vol. 16, No. 1, Jan. 19, 2010, pp. 44-49.
Official Communication issued in European Patent Office (EPO) Patent Application No. 17861732.0, dated Apr. 20, 2020.
Office Action issued in CHINA Counterpart Patent Appl. No. 201780077827.4, dated Apr. 9, 2021, along with an English translation thereof.
Japan Office Action received in JP Applications No. 2018-546332, dated Oct. 6, 2021 and English translation thereof.

* cited by examiner

MEDICAL USE HONEYCOMB STRUCTURE

TECHNICAL FIELD

The present invention relates to a medical use material and a method for producing the same. More specifically, the present invention relates to a medical use material having a honeycomb structure for use in tissue regeneration/reconstruction techniques for bones, teeth, and the like or in scaffolds and the like for regenerative medicine in the medical field or fields related to medicine, and a method for producing the same.

BACKGROUND ART

In the clinical practice of medicine and dentistry, defective tissues may be regenerated or reconstructed with medical materials. At that time, it may be expected that medical materials bind to surrounding tissues. An important initial step such as the binding of medical materials to surrounding tissues is the adhesion of cells or the binding of tissues to material surfaces. The conduction of tissues or the migration of cells is unlikely to occur unless medical materials are fixed to surrounding tissues.

Among the medical materials, since cells or tissues can easily penetrate to the interior of porous materials, the porous materials often exhibit excellent functions. The porous materials are classified into closed-pore porous materials and interconnected porous materials. In case of expecting replacement of tissues with medical materials, interconnected porous materials in which cells can penetrate to the interior of the materials are highly useful. Hence, a method for producing an interconnected porous material by introducing and incinerating a pore forming material has been proposed as disclosed in Patent Literatures 1 and 2.

Meanwhile, as reported in Non Patent Literature 1, tissues such as bones are variously oriented depending on sites, and such orientation of tissues has been found to improve functions. However, as pointed out in Non Patent Literatures 2 and 3, etc., regenerated bones are poorly orientational and poorly functional. Therefore, it has been pointed out that inducing orientation is necessary.

As for orientational interconnected porous materials, a production method applying the principle of ice columns has been proposed as disclosed in Patent Literatures 3 to 7. However, the orientational interconnected porous materials produced by applying the principle of ice columns are not always sufficiently orientational. Furthermore, strict temperature control is necessary for the growth of ice columns, resulting in poor productivity and a high production cost. Moreover, there are big problems such as the impossibility of producing orientational interconnected porous materials having exactly the same forms.

Meanwhile, honeycomb structures produced by extrusion molding or the like reported in Patent Literatures 8 and 9, etc. exhibit ideal orientational interconnected porous materials. However, the honeycomb structures produced heretofore do not always exhibit the sufficient ability to bind to tissues or to adhere to cells and are not medical materials satisfactory for tissue regeneration/reconstruction.

Hence, Patent Literature 10 discloses a technique of forming a plurality of grooves on the surface of a substrate section formed into a plate-shape by cutting a honeycomb structure at its plane parallel to a through-hole direction. The technique disclosed in Patent Literature 10, as compared with honeycomb structures that maintain an outer peripheral side wall, is excellent in the adhesiveness or binding of cells or tissues to a material surface, but is not sufficient in terms of functions such as binding to surrounding tissues because cells or tissues cannot penetrate to the interior of the honeycomb structure from the outer peripheral side wall.

Patent Literature 11 discloses a technique of making a hole that passes through an outer peripheral side wall of a honeycomb structure. This allows cells or tissues to penetrate to the interior of the honeycomb structure from the outer peripheral side wall. Hence, the technique disclosed in Patent Literature 11, as compared with honeycomb structures having no hole in an outer peripheral side wall, is excellent in the adhesiveness or binding of cells or tissues to a material surface, but requires a very high production cost. Furthermore, the ability of an outer peripheral surface to bind to surrounding tissues was not sufficient. Moreover, the orientation of surrounding tissues in the outer peripheral side wall was totally uncontrollable.

CITATION LIST

Patent Literatures

Patent Literature 1: Japanese Patent No. 3470759
Patent Literature 2: Japanese Patent No. 4802317
Patent Literature 3: Japanese Patent No. 3858069
Patent Literature 4: Japanese Patent No. 3940770
Patent Literature 5: Japanese Patent Laid-Open Publication No. 2008-230910
Patent Literature 6: Japanese Patent Laid-Open Publication No. 2010-18459
Patent Literature 7: Japanese Patent Laid-Open Publication No. 2012-148929
Patent Literature 8: Japanese Patent Laid-Open Publication No. 2004-298407
Patent Literature 9: Japanese Patent Laid-Open Publication No. 2005-152006
Patent Literature 10: Japanese Patent Laid-Open Publication No. 2004-298545
Patent Literature 11: Japanese Patent Laid-Open Publication No. 2005-110709

Non Patent Literatures

Non Patent Literature 1: Nakano T. et al., "Unique alignment and texture of biological apatite crystallites in typical calcified tissues analyzed by micro-beam X-ray diffractometer system", Bone, 31 [4] (2002) 479-487
Non Patent Literature 2: Nakano T. et al., "Biological apatite (BAp) crystallographic orientation and texture as a new index for assessing the microstructure and function of bone regenerated by tissue engineering", Bone 51 (2012) 741-747
Non Patent Literature 3: Ishimoto T. et al., "Degree of biological apatite c-axis orientation rather than bone mineral density controls mechanical function in bone regenerated using rBMP-2", Journal of Bone and Mineral Research 28 (2013) 1170-1179

SUMMARY OF INVENTION

Technical Problem

According to the method for producing an interconnected porous material by introducing and incinerating a pore forming material as described above, a non-orientational porous material, a poorly orientational porous material, or a porous material having non-interconnected pores was produced.

The orientational interconnected porous materials produced by applying the principle of ice columns were not sufficiently orientational. Furthermore, strict temperature control is necessary for the growth of ice columns, and there are problems such as poor productivity, a high production cost, and the impossibility of producing uniaxially orientational interconnected porous materials having exactly the same forms.

The honeycomb structures produced by extrusion molding or the like are ideal orientational interconnected porous materials and have therefore been expected to provide excellently orientational medical materials. However, the previously provided honeycomb structures do not always exhibit the sufficient ability to adhere to cells, to bind to tissues, or to form oriented tissues and cannot be produced at a practicable production cost.

The present invention has been made in light of the problems as described above. Objective of the present invention is to provide a medical use honeycomb structure that satisfies the demands desired of a medical use material, namely: (1) having excellent adhesiveness or binding of a cell or a tissue to a material surface; (2) can regenerate/reconstruct an oriented tissue; (3) having excellent mechanical strength; (4) when used as a tissue replacement material, quickly replacing a desired tissue; and (5) being able to be produced at a low cost, and a method for producing the same.

Solution to Problem

The present inventors have conducted diligent studies and consequently completed the present invention by finding that a medical use material that satisfies the demands (1) to (5) described above is attained by forming a through-hole groove formed by scraping a side wall of a through-hole constituting the honeycomb structure, and a through-hole inlet adjacent to the through-hole groove, in an outer peripheral section of a honeycomb structure comprising a plurality of through-holes extending in one direction.

Specifically, the present invention is as follows.

[1] A medical use honeycomb structure comprising a plurality of through-holes extending in one direction (in a single direction), wherein an outer peripheral section of the medical use honeycomb structure has a through-hole groove formed by scraping a side wall of the through-hole, and a through-hole inlet adjacent to the through-hole groove.

[2] The medical use honeycomb structure according to [1], wherein an inclined surface which is inclined with respect to a penetrating direction of the through-hole is formed.

[3] The medical use honeycomb structure according to [1] or [2], wherein a ratio of a length in a longitudinal direction to a length in a width direction of the through-hole groove is 1.5 or more.

[4] The medical use honeycomb structure according to any one of [1] to [3], wherein a ratio of the number of through-hole inlets to the number of through-holes in an outermost layer is 0.05 or more.

[5] The medical use honeycomb structure according to any one of [1] to [4], wherein the through-hole groove and the through-hole inlet are provided in at least an outermost layer and a second outer layer in an inner side thereof.

[6] The medical use honeycomb structure according to any one of [1] to [5], wherein a percentage of a concave-convex surface provided with the through-hole groove and the through-hole inlet on an outer peripheral side surface is 10% or more.

[7] The medical use honeycomb structure according to any one of [1] to [6], wherein a piercing hole which pierces the side wall of the through-hole is provided.

[8] The medical use honeycomb structure according to any one of [1] to [7], wherein a diameter of the through-hole is 5 µm or larger and 400 µm or smaller.

[9] The medical use honeycomb structure according to any one of [1] to [8], wherein a thickness of a partition wall of the through-hole is 10 µm or larger and 300 µm or smaller.

[10] The medical use honeycomb structure according to any one of [1] to [9], wherein a ratio of a diameter of the through-hole to a thickness of a partition wall of the through-hole is 0.2 or more and 20 or less.

[11] The medical use honeycomb structure according to any one of [1] to [10], wherein a thickness of an outer peripheral side wall of the outer peripheral section is 300 µm or smaller.

[12] The medical use honeycomb structure according to any one of [1] to [11], wherein a ratio of a length in a longitudinal direction to a diameter of the through-hole is 3 or more.

[13] The medical use honeycomb structure according to any one of [1] to [12], wherein the medical use honeycomb structure is a block of $10^{-8}$ m$^3$ or larger and $10^{-3}$ m$^3$ or smaller.

[14] The medical use honeycomb structure according to any one of [1] to [13], wherein the medical use honeycomb structure is made of a composition containing at least a calcium compound.

[15] The medical use honeycomb structure according to [14], wherein the calcium compound is at least one member selected from the group consisting of calcium phosphate, calcium carbonate, calcium sulfate and calcium-containing glass.

[16] The medical use honeycomb structure according to any one of [1] to [15], wherein the medical use honeycomb structure is made of a composition containing at least one type selected from the group consisting of apatite, β-tricalcium phosphate, α-tricalcium phosphate and octacalcium phosphate.

[17] The medical use honeycomb structure according to any one of [1] to [16], wherein the medical use honeycomb structure is made of a composition containing carbonate apatite.

[18] The medical use honeycomb structure according to any one of [1] to [17], wherein the medical use honeycomb structure is made of a composition containing a polymer material.

[19] A crushed product of a medical use honeycomb structure according to any one of [1] to [18].

[20] The crushed product according to [19], wherein the crushed product has a size of $10^{-12}$ m$^3$ or larger and smaller than $10^{-8}$ m$^3$.

[21]

A medical use honeycomb structure comprising a plurality of through-holes extending in one direction, wherein the medical use honeycomb structure is made of a composition containing carbonate apatite.

[22] A crushed product of a medical use honeycomb structure according to [21].

[23] A method for producing a medical use honeycomb structure according to any one of [1] to [18], comprising:

an outer-walled structure preparation step of extruding a material through a die for forming honeycomb structure to prepare a honeycomb structure having an outer peripheral side wall; and an outer peripheral section processing step of removing at least a portion of the outer peripheral side wall of the honeycomb structure having an outer peripheral side wall to form a through-hole groove and a through-hole inlet in an outer peripheral section.

[24] A method for producing a medical use honeycomb structure crushed product according to [19] or [20], comprising:

an outer-walled structure preparation step of extruding a material through a die for forming a honeycomb structure to prepare a honeycomb structure having an outer peripheral side wall;

an outer peripheral section processing step of removing at least a portion of the outer peripheral side wall of the honeycomb structure having an outer peripheral side wall to form a through-hole groove and a through-hole inlet in an outer peripheral section; and a crushing step of crushing the honeycomb structure formed with the through-hole groove and the through-hole inlet into a size of $10^{-12}$ m$^3$ or larger and smaller than $10^{-8}$ m$^3$.

[25] A method for producing a medical use honeycomb structure according to any one of [1] to [17] comprising carbonate apatite in composition, comprising:

an outer-walled structure preparation step of extruding a mixture of calcium hydroxide mixed with an organic binder through a die for forming a honeycomb structure to prepare a honeycomb structure having an outer peripheral side wall;

a debindering step of debindering the honeycomb structure;

a carbonation step of performing a carbonation treatment of the honeycomb structure simultaneously with or subsequently to the debindering step; and an apatite preparation step of adding an aqueous phosphate solution to the honeycomb structure that has undergone the carbonation step, wherein the method comprises, at any stage after the outer-walled structure preparation step, an outer peripheral section processing step of removing at least a portion of the outer peripheral side wall of the honeycomb structure having an outer peripheral side wall to form a through-hole grooves and a through-hole inlet in an outer peripheral section.

[26]

A method for producing a medical use honeycomb structure according to any one of [1] to [17] comprising carbonate apatite in composition, comprising:

an outer-walled structure preparation step of extruding a mixture of calcium sulfate mixed with an organic binder through a die for forming a honeycomb structure to prepare a honeycomb structure having an outer peripheral side wall;

a debindering step of debindering the honeycomb structure; and an apatite preparation step of adding an aqueous solution containing a carbonate and a phosphate or sequentially adding an aqueous solution containing a carbonate and an aqueous solution containing a phosphate to the honeycomb structure that has undergone the debindering step, wherein the method comprises, at any stage after the outer-walled structure preparation step, an outer peripheral section processing step of removing at least a portion of the outer peripheral side wall of the honeycomb structure having an outer peripheral side wall to form through-hole grooves and through-hole inlets in an outer peripheral section.

[27]

A method for producing a medical use honeycomb structure according to [21], comprising:

an outer-walled structure preparation step of extruding a mixture of calcium hydroxide mixed with an organic binder through a die for forming a honeycomb structure to prepare a honeycomb structure having an outer peripheral side wall;

a debindering step of debindering the honeycomb structure;

a carbonation step of performing a carbonation treatment of the honeycomb structure simultaneously with or subsequently to the debindering step; and an apatite preparation step of adding an aqueous phosphate solution to the honeycomb structure that has undergone the carbonation step.

[28]

A method for producing a medical use honeycomb structure according to [21], comprising:

an outer-walled structure preparation step of extruding a mixture of calcium sulfate mixed with an organic binder through a die for forming a honeycomb structure to prepare a honeycomb structure having an outer peripheral side wall;

a debindering step of debindering the honeycomb structure; and an apatite preparation step of adding an aqueous solution containing a carbonate and a phosphate or sequentially adding an aqueous solution containing a carbonate and an aqueous solution containing a phosphate to the honeycomb structure that has undergone the debindering step.

Advantageous Effects of Invention

The medical use honeycomb structure of the present invention satisfies demands desired of a medical use material, namely: (1) having excellent adhesiveness or binding of a cell or a tissue to a material surface; (2) can regenerate/reconstruct an oriented tissue; (3) having excellent mechanical strength; (4) when used as a tissue replacement material, quickly replacing a desired tissue; and (5) being able to be produced at a low cost, and is widely applicable in the medical field or fields related to medicine.

BRIEF DESCRIPTION OF DRAWINGS

FIG. 6 is a photograph of a cylindrical binder-containing calcium hydroxide honeycomb structure having an outer peripheral side wall, prepared as an intermediate according to Example 1a.

FIG. 7 is a photograph of a honeycomb structure before a debindering step according to Example 1a.

FIG. 8 is an electron microscope photograph (SEM photograph) of a honeycomb structure after the debindering step according to Example 1a.

FIG. 9(a) is an image of the honeycomb structure cut vertically to through-holes (cells), and FIG. 9(b) is an image of the honeycomb structure cut parallelly to through-holes (cells).

FIG. 17 is an electron microscope photograph (SEM photograph) of a honeycomb structure according to Example 11a.

DESCRIPTION OF EMBODIMENTS

[Medical Use Honeycomb Structure of the Present Invention]

The medical use honeycomb structure of the present invention is a medical use honeycomb structure comprising a plurality of through-holes (hollow bodies) extending in one direction, wherein an outer peripheral section of the medical use honeycomb structure has through-hole grooves formed by incomplete side walls of the through-holes, and through-hole inlets adjacent to the through-hole grooves.

Hereinafter, each configuration will be described.

<Honeycomb Structure of the Medical Use Honeycomb Structure of the Present Invention>

The medical use honeycomb structure of the present invention has a honeycomb structure. The honeycomb structure according to the present invention refers to a structure of through-type polygonal hollow columns or through-type round hollow columns (through-holes) passing through in the long axis direction arranged without space. A space formed by this through-hole and both ends of the through-hole is referred to as a cell.

The orientational interconnected porous materials produced by exploiting the principle of ice columns as disclosed in Patent Literatures 3 to 7 cannot form the honeycomb structure of the present invention described above because ice columns forming the pores are linked in the course of formation or the growth of the ice columns is inhibited by the growth of other ice columns. Thus, the orientational interconnected porous materials produced by exploiting the principle of ice columns as disclosed in Patent Literatures 3 to 7 are not included in the medical use honeycomb structure of the present invention.

The honeycomb structure of the present invention can usually be formed by extrusion molding or the like. Specifically, for example, a hydroxyapatite powder is mixed with an organic binder, and the mixture can be extrusion-molded by, for example, a method disclosed in Japanese Patent No. 3405536 or Japanese Patent Laid-Open Publication No. 10-59784 to produce a honeycomb structure having an outer peripheral side wall (precursor of the honeycomb structure of the present invention) and comprising hydroxyapatite and the organic binder in composition. Further, a carbonate apatite powder is extrusion-molded with collagen as a binder, and the extrudate is dried to produce a honeycomb structure having an outer peripheral side wall (precursor of the honeycomb structure of the present invention) and comprising carbonate apatite and collagen in composition. By removing the outer peripheral side wall of this honeycomb structure having an outer peripheral side wall to form through-hole grooves and through-hole inlets in the outer peripheral section, the medical use honeycomb structure of the present invention can be obtained.

Figure 1:
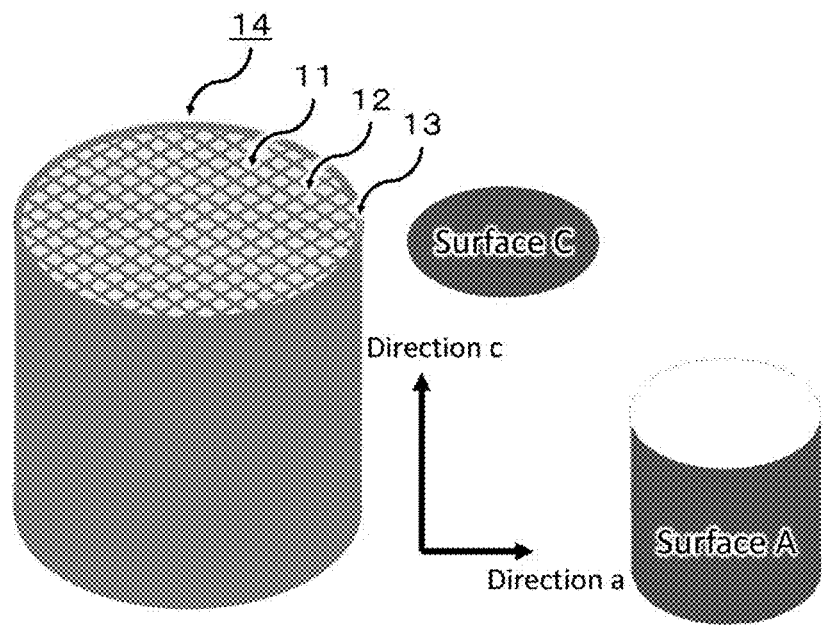
FIG. 1 is a schematic view of a honeycomb structure having an outer peripheral side wall.

Here, one example of the honeycomb structure having an outer peripheral side wall, which is a precursor of the honeycomb structure of the present invention, will be described with reference to FIG. 1. As shown in FIG. 1, honeycomb structure 14 having an outer peripheral side wall is a cylindrical object comprising a plurality of through-holes 11 extending in one direction, partition walls 12 which partition the through-holes, and outer peripheral side wall 13 which surrounds a honeycomb structure section consisting of the through-holes. Hereinafter, if necessary, a direction perpendicular to the penetrating direction of the through-holes is referred to as direction a; the surface of the outer peripheral side wall is referred to as surface A; the penetrating direction of the through-holes is referred to as direction c; and a surface formed by the ends of the through-holes is referred to as surface C. For example, when the honeycomb structure has a cylindrical shape as shown in FIG. 1, the surface A is the side surface of the cylindrical shape, and the surface C is a circle.

<Honeycomb Structure Outer Peripheral Side Wall>

Figure 2:
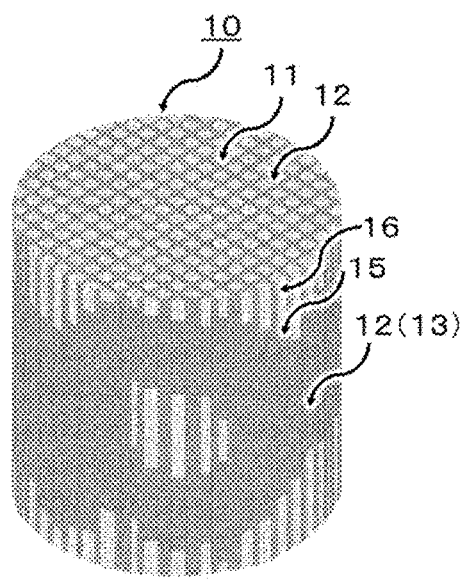
FIG. 2 is a schematic view (one example) of the medical use honeycomb structure of the present invention.
Figure 3:
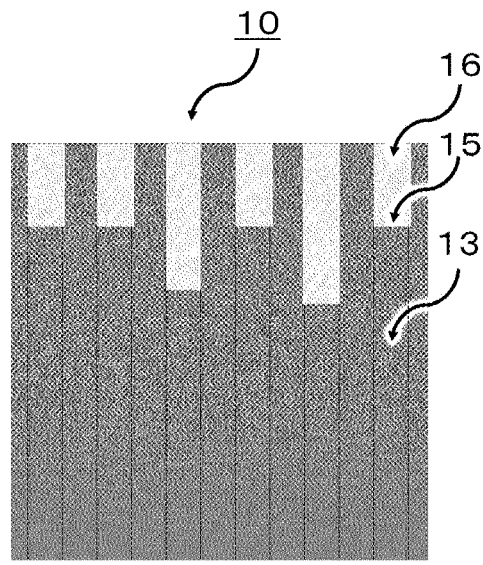
FIG. 3 is a schematic view (one example) showing a state where a portion of an outer peripheral side wall of the medical use honeycomb structure of the present invention has been removed.

FIG. 2 shows a schematic view (one example) of the medical use honeycomb structure of the present invention. The honeycomb structure 14 shown in FIG. 1 is shown in a state where the outer peripheral side wall has been removed. In this medical use honeycomb structure 10, the outer peripheral side wall (outer peripheral section) of the honeycomb structure having the outer peripheral side wall 13 is removed by grinding, cutting, or the like to form through-hole grooves 16 and through-hole inlets 15 in the outer peripheral section. Here, FIG. 3 is a schematic view showing a state where a portion of the outer peripheral side wall of the medical use honeycomb structure has been removed according to another example of the present invention.

Figure 4:
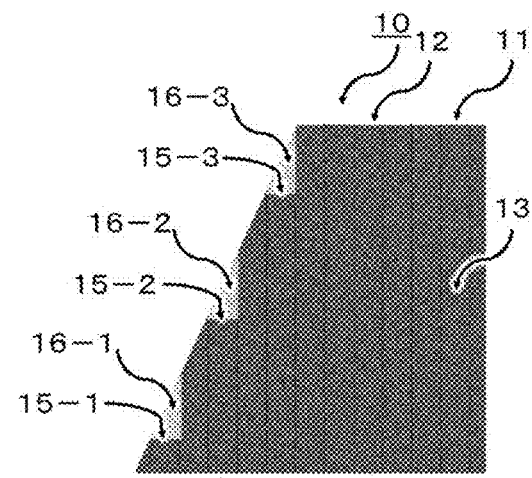
FIG. 4 is a schematic view (one example) showing a state where a plurality of layers in an outer peripheral side wall of the medical use honeycomb structure of the present invention have been removed.

Through-hole grooves 16 having various lengths are formed, and through-hole inlets 15 are formed adjacently to the through-hole grooves 16. For example, as shown in FIG. 4, by cutting or the like at an angle, an inclined surface is formed in the outer peripheral section, and at the same time through-hole grooves 16 and through-hole inlets 15 are formed. By providing such an inclined surface, the through-hole grooves and the through-hole inlets can be formed not only to the outermost layer of the honeycomb structure but to a plurality of layers in the inner side of the outermost layer.

The inclined surface formed in the outer peripheral section of the medical use honeycomb structure of the present invention refers to a surface inclined with respect to the penetrating direction of the through-holes, and a plurality of inclined surfaces may be formed in step-like manner. The inclination angle is an angle capable of forming the through-hole grooves and the through-hole inlets, and as such conditions, for example, the tangent of the angle formed by the inclined surface and the penetrating direction is a value larger than a value obtained by dividing the thickness of the outer peripheral side wall or of the partition wall by the length in the through-hole direction of the honeycomb structure.

In the present invention, the thickness of the outer peripheral side wall is the part of the honeycomb structure 14 shown in FIG. 1 from which a plurality of the through-holes 11 extending in one direction and the partition walls 12 which partition the through-holes are excluded, i.e., the thickness of the outer peripheral side wall 13 which surrounds a honeycomb structure section consisting of the through-holes. When the thickness of the outer peripheral is not uniform, the thickness of the thickest moiety is regarded as the thickness of the outer peripheral side wall.

In the present invention, the thickness of the partition wall is the thickness of the partition walls 12 which partition the through-holes in the honeycomb structure 14 shown in FIG. 1. When the thickness of partition is not uniform, the smallest thickness among the thicknesses of the partition walls which isolate adjacent through-holes from each other is regarded as the thickness of the partition wall.

Although it is preferred to provide an inclined surface in the outer peripheral section, it is not necessarily required to provide such an inclined surface. For example, when a first surface and a second surface parallel to the penetrating direction of the through-holes are formed in a portion of the outer peripheral section, the through-hole grooves and the through-hole inlets can be formed by forming the first surface and the second surface such that the difference between the distances of the first surface and the second surface from the central portion of the honeycomb structure is a value larger than the thickness of the partition wall.

The thickness of the outer peripheral side wall is preferred to be a smaller thickness in a range that permits molding such as extrusion molding, and is preferably 300 μm or smaller, more preferably 200 μm or smaller, further preferably 150 μm or smaller.

In the medical use honeycomb structure of the present invention, the percentage of a concave-convex surface (surface where grinding or cutting is performed) provided with the through-hole grooves and the through-hole inlets on the outer peripheral side surface is preferably 10% or more, more preferably 50% or more, further preferably 80% or more, particularly preferably 95% or more, most preferably 100%, of the area of the outer peripheral side surface from the viewpoint of facilitating tissue penetration from tissues surrounding the honeycomb structure to the interior of the honeycomb structure.

<Through-Hole Inlet>

In a usual honeycomb structure obtained by extrusion molding, the outer peripheral section is covered by a smooth outer peripheral side wall 13 as shown in FIG. 1. In the present invention, at least a portion of the outer peripheral side wall is removed to expose the interior through-holes (honeycomb structure section) to the outer peripheral side surface. In the present invention, the inlet at the ends of the through-holes exposed to the outer peripheral side surface are referred to as through-hole inlets. The through-hole inlets are inlets at the ends of the through-holes exposed to the outer peripheral side surface and are distinguished from inlets at the terminal ends of the through-holes originally present on the surface C without removing the outer peripheral side wall.

<Through-Hole Groove>

Figure 5:
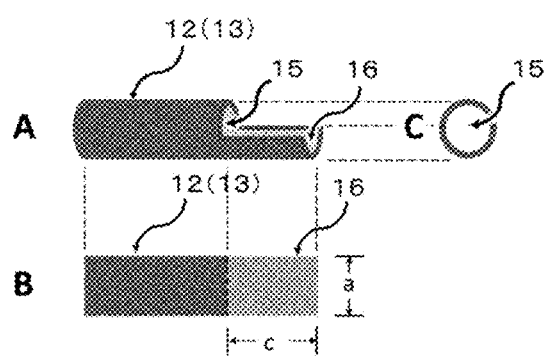
FIG. 5 is a view illustrating a through-hole groove and a through-hole inlet in the medical use honeycomb structure of the present invention.

As in the above-mentioned through-hole inlets, by removing at least a portion of the outer peripheral side wall, grooves are formed when cutting (scraping) side walls of the through-holes. In the present invention, these grooves are referred to as through-hole grooves. The side walls of the through-holes include both the outer peripheral side wall and the partition wall. In the present invention, the ratio of the length (indicated by c of FIG. 5) in the longitudinal direction with respect to the length (indicated by a of FIG. 5) in the width direction of the through-hole groove (groove aspect ratio c/a) is important for forming tissues oriented to the outer peripheral section of the honeycomb structure. The groove aspect ratio is preferably 1.5 or more, more preferably 2.0 or more, further preferably 3.0 or more, particularly preferably 4.0 or more. The through-hole groove of the present invention includes a groove in which the side section over the entire length of the through-hole is scraped (groove over the entire length of the through-hole).

<Positions of Through-Hole Inlet and Through-Hole Groove in the Medical Use Honeycomb Structure of the Present Invention>

In the case of the honeycomb structure of the present invention, not only the tissues penetrate the interior of the honeycomb structure from the surface C, but surrounding tissues, for example, penetrate the interior of the honeycomb structure from the through-hole inlets formed in the outer peripheral section of the honeycomb structure so that the surrounding tissues bind to the honeycomb structure by an engaging force. Hence, it is more preferred to form the through-hole inlets not only in the outermost layer of the honeycomb structure but in a plurality of layers such as a second outer layer, a third outer layer, and a fourth outer layer in the inner side thereof. Specifically, when the through-hole inlets are formed not only in the outermost layer of the honeycomb structure but in interior layers as shown in FIG. 4, the binding ability of tissues to a material surface is further ensured because the binding is ensured not only by the tissues surrounding the honeycomb structure and the oriented tissues that have penetrated the interior of the through-holes in the outermost layer of the honeycomb structure by the oriented tissues to be penetrated, but by the oriented tissues that have penetrated the interior of the through-holes in the inner side of the outermost layer of the honeycomb structure.

FIG. 4 is a schematic view showing a state where a plurality of layers in the outer peripheral side wall of the honeycomb structure of the present invention have been removed. Reference numeral 15-1 represents a through-hole inlet in the outermost layer (most distant section from the central through-hole); reference numeral 15-2 represents a through-hole inlet in the second outer layer (second most distant section following the through-hole inlet 15-1 when viewed from the central through-hole); and reference numeral 15-3 represents a through-hole inlet in the third outer layer (third most distant section following the through-hole inlet 15-2 when viewed from the central through-hole). Reference numerals 16-1, 16-2, and 16-3 represent through-hole grooves continuous with the through-hole inlets 15-1, 15-2, and 15-3, respectively. Such configuration can be easily formed by providing an inclined surface in the outer peripheral section.

<Abundance Ratio of Through-Hole Inlet>

In the medical use honeycomb structure of the present invention, a larger number of through-hole inlets is more preferred. Since the preferred number of through-hole inlets depends on the size of the honeycomb structure, the abundance ratio of the through-hole inlets is indicated by the ratio of the number of through-hole inlets to the number of through-holes in the outermost layer. In the present invention, the through-hole inlet abundance ratio is preferably 0.05 or more, more preferably 0.1 or more, further preferably 0.4 or more, particularly preferably 0.5 or more, most preferably 1.0 or more.

As for the number of through-hole inlets, a plurality of through-hole inlets may be provided per through-hole by a method of, for example, providing a plurality of inclined surfaces or a plurality of removed surfaces in the outer peripheral section, and this approach is very useful. In such a case, the through-hole inlet abundance ratio is preferably 1.0 or more, more preferably 1.3 or more, further preferably 1.6 or more, still further preferably 2.0 or more.

<Piercing Hole which Pierces Side Walls (Partition Wall and Outer Peripheral Side Wall) of Through-Holes>

The honeycomb structure is ideal for imparting orientation to the tissues to be formed, but has the disadvantage of poor binding between formed tissues except for the case of using a material that will replace the tissue such as carbonate apatite. Hence, for imparting three-dimensional continuity to tissues to be formed while imparting orientation to the tissues to be formed, it may be effective to provide a piercing hole which pierces the side walls (partition walls and outer peripheral side wall) of the through-holes, in addition to the through-hole grooves and the through-hole inlets in the outer peripheral section. Particularly, it is preferred to provide a piercing hole in the outer peripheral side wall. The penetrating hole which pierces a plurality of side walls (partition walls and outer peripheral side wall) can be formed by, for example, drilling.

<Shape of Cell Cross Section (Through-Hole Cross Section) and Diameter of Cell (Through-Hole) in Honeycomb Structure>

The cell cross section in the honeycomb structure of the medical use honeycomb structure of the present invention is a polygon or a circle.

The diameter of the through-hole in the medical use honeycomb structure of the present invention is preferably 5 µm or larger and 400 µm or smaller, more preferably 10 µm or larger and 300 µm or smaller, further preferably 20 µm or larger and 250 µm or smaller. The diameter of the through-hole is the length of the diameter of a circle, for example, when the cross section is a circle, and is the length of a diagonal line when the cross section is a polygon such as a square.

This diameter of the cross section is used in the calculation of the aspect ratio of the cells (through-holes). The ratio of the length in the longitudinal direction to the diameter of the through-hole (cell aspect ratio) is preferably 3 or more, more preferably 5 or more, further preferably 10 or more, from the viewpoint of the adhesion of cells and oriented tissue formation.

<Thickness of Partition Wall of Through-Hole>

The thickness of the partition wall of the through-hole in the medical use honeycomb structure of the present invention is a factor that influences the mechanical strength of the honeycomb structure, the tissue replacement rate of the medical use honeycomb structure, etc.

Specifically, a larger thickness of the partition wall increases the mechanical strength of the medical use honeycomb structure and on the other hand, slows down tissue replacement with the medical use honeycomb structure, for example, in the case of a medical use honeycomb structure comprising bone-replacing carbonate apatite in composition.

For example, in the case of immersing a calcium carbonate honeycomb structure in an aqueous phosphate solution to convert it to a medical use carbonate apatite honeycomb structure through dissolution-precipitation-type compositional conversion reaction, there are problems such that when the thickness of the partition wall is large, the reaction will be time-consuming because the dissolution-precipitation-type compositional conversion reaction progresses from the surface of the precursor, and a carbonate apatite honeycomb structure cannot be produced, if it is not produced at a high temperature such as hydrothermal reaction. For example, a carbonate apatite honeycomb structure produced at a high temperature such as hydrothermal conditions is highly crystalline and inferior in tissue reactions such as osteoconductive properties as compared with a carbonate apatite honeycomb structure produced at a temperature of 100° C. or lower. Therefore, the thickness of the partition wall is very important.

Since their balance is important, the thickness of the partition wall of the through-hole in the medical use honeycomb structure is preferably 10 µm or larger and 300 µm or smaller, more preferably 20 µm or larger and 200 µm or smaller, further preferably 30 µm or larger and 150 µm or smaller.

In the case of producing a medical use carbonate apatite honeycomb structure of the present invention comprising carbonate apatite in composition, and having better tissue compatibility such as osteoconductive properties as the medical use honeycomb structure, the thickness of the partition wall is preferably 10 µm or larger and 200 µm or smaller, more preferably 20 µm or larger and 150 µm or smaller, further preferably 30 µm or larger and 100 µm or smaller.

<Ratio of Through-Hole Diameter to Thickness of Partition Wall>

In addition to the thickness of the partition wall in the medical use honeycomb structure of the present invention, the size of the through-hole as a cell is also a factor that influences the mechanical strength of the honeycomb structure, the tissue replacement rate of the medical use honeycomb structure, etc.

A larger ratio of the through-hole diameter (diameter of the through-hole cross section) to the thickness of the partition wall increases the porosity of the medical use honeycomb structure and facilitates the penetration of cells or tissues to the interior thereof, while decreases the mechanical strength of the medical use honeycomb structure. In consideration of their balance, the ratio of the through-hole diameter to the thickness of the partition wall in the honeycomb structure is preferably 0.2 or more and 20 or less, more preferably 0.25 or more and 10 or less, further preferably 0.5 or more and 5 or less.

<Size (Volume) of Honeycomb Structure>

The outer size of the medical use honeycomb structure (block) of the present invention is preferably $10^{-8}$ m$^3$ or larger and $10^{-3}$ m$^3$ or smaller, more preferably $7\times10^{-5}$ m$^3$ or larger and $4\times10^{-4}$ m$^3$ or smaller.

The outer size of the medical use honeycomb structure of the present invention is obtained by measuring the length of the honeycomb structure, followed by calculation. For example, when the honeycomb structure is cylindrical, the length of the diameter of the surface C which is a circle and the length in the through-hole direction of the surface C are measured, and the outer size is calculated from the two lengths. At that time, by measuring the weight of the honeycomb structure, by dividing the weight by the volume, the apparent density of the honey comb structure can be obtained. As such, the volume can be calculated from the weight of a honeycomb structure crushed product (granules).

<Honeycomb Structure Crushed Product (Granules)>

The crushed product of the medical use honeycomb structure of the present invention is obtained by crushing the medical use honeycomb structure in a block form described above. The size (outer) of the crushed product is preferably $10^{-12}$ m$^3$ or larger and smaller than $10^{-8}$ m$^3$, more preferably $4\times10^{-12}$ m$^3$ or larger and smaller than $10^{-8}$ m$^3$, further preferably $6\times10^{-12}$ m$^3$ or larger and smaller than $10^{-8}$ m$^3$.

As described above, the size (outer) of the honeycomb structure crushed product (granules) can be determined by dividing the weight of the honeycomb structure crushed product (granules) by the apparent density of the uncrushed honeycomb structure used in the production of the honeycomb structure crushed product (granules).

<Composition>

The composition (material) of the medical use honeycomb structure is not particularly limited and preferably comprises at least a calcium compound excellent in cell compatibility or tissue compatibility. Although the mechanism why a calcium-containing compound is preferred for the composition of the medical use honeycomb structure has not yet been fully understood, it is probably preferred to comprise a calcium-containing compound in composition because calcium plays an important role in cell adhesion.

In the present invention, among calcium compounds, at least one member selected from the group consisting of calcium phosphate, calcium carbonate, calcium sulfate and calcium-containing glass is preferred. Calcium phosphate contains a phosphoric acid component in addition to calcium and is preferred because the phosphoric acid component also plays an important role in cell adhesion and the like. Calcium carbonate and calcium sulfate are preferred because they exhibit solubility appropriate for calcium supply to cells.

The calcium phosphate according to the present invention is a salt of phosphoric acid and calcium, and examples thereof can include calcium orthophosphate, calcium metaphosphate, and calcium condensed phosphate. Among the calcium phosphates, calcium orthophosphate is preferred because it exhibits relatively excellent osteoconductive properties and tissue compatibility. The calcium orthophosphate according to the present invention refers to a salt of orthophosphoric acid and calcium, and examples thereof can include tetracalcium phosphate, apatite including hydroxyapatite and carbonate apatite, α-tricalcium phosphate, β-tricalcium phosphate, and octacalcium phosphate.

Among the calcium phosphates, at least one type selected from the group consisting of apatite such as carbonate apatite, β-tricalcium phosphate (β-TCP), α-tricalcium phosphate, and octacalcium phosphate is more preferred.

The carbonate apatite according to the present invention is apatite in which a portion or the whole of phosphoric acid or hydroxy groups of apatite is substituted by a carbonic acid group. Apatite with the hydroxy group substituted by a carbonic acid group is referred to as type-A carbonate apatite. Apatite with the phosphoric acid group substituted by a carbonic acid group is referred to as type-B carbonate apatite. Apatite with both the groups substituted by a carbonic acid group is referred to as type-AB carbonate apatite. Na, K, or the like is often contained in the crystal structure as the phosphoric acid group is substituted by a carbonic acid group. A compound in which a portion of carbonate apatite is substituted by a different element or a void is also included in the carbonate apatite of the present invention.

The honeycomb structure made of this carbonate apatite has the advantage that a relatively large size may also be produced.

For example, a method for producing a medical use bone prosthetic material composed mainly of carbonate apatite, disclosed in Japanese Patent No. 4854300 produces a carbonate apatite block by immersing a calcium carbonate block which is a precursor in an aqueous phosphate solution. This reaction is dissolution-precipitation reaction through which the precursor calcium carbonate is dissolved in the aqueous solution to liberate $Ca^{2+}$ and $CO_3^{2-}$ into the aqueous solution. When a phosphate is present in the aqueous solution, the aqueous solution containing $Ca^{2+}$ and $CO_3^{2-}$ coexisting with $PO_4^{3-}$ is supersaturated to carbonate apatite to form precipitates on the surface of the precursor. Thus, while the precursor calcium carbonate maintains basic composition, the composition is converted to carbonate apatite through dissolution-precipitation reaction. The dissolution-precipitation reaction progresses from the surface of the precursor to the interior. Therefore, when the precursor is a dense body, the reaction time is drastically prolonged with increase in depth from the surface of the precursor.

For a porous material such as a foam disclosed in Japanese Patent No. 4854300, even in the case of having a large apparent size as a whole, compositional conversion through dissolution-precipitation reaction terminates in a relatively short time because an aqueous phosphate solution penetrates the interior so that dissolution-precipitation reaction progresses from the interior surface of the material.

As seen from this reaction mechanism, $Ca^{2+}$, $CO_3^{2-}$, and $PO_4^{3-}$ need to coexist with each other on the material surface in the precipitation reaction. When the calcium carbonate block is a dense body, precipitation reaction is relatively unlikely to occur because $Ca^{2+}$ and $CO_3^{2-}$ eluted from the material surface disappear from the material surface by diffusion. On the other hand, since a foam or the like is a porous material, $Ca^{2+}$ and $CO_3^{2-}$ eluted from the trabecular surface of the foam disappear less from the material surface by diffusion, as compared with a block without interconnected pores.

When the porous material is a honeycomb structure, the disappearance of $Ca^{2+}$ and $CO_3^{2-}$ eluted from honeycomb partition walls, from the material surface by diffusion is very limited because the honeycomb is a porous material having through-holes in a uniaxial direction. Hence, use of a precursor of the honeycomb structure permits preparation of a carbonate apatite block having a large size.

The apatite according to the present invention is a compound having $A_{10}(BO_4)_6C_2$ as a basic structure. Examples of A include $Ca^{2+}$, $Cd^{2+}$, $Sr^{2+}$, $Ba^{2+}$, $Pb^{2+}$, $Zn^{2+}$, $Mg^{2+}$, $Mn^{2+}$, $Fe^{2+}$, $Ra^{2+}$, $H^+$, $H_3O^+$, $Na^+$, $K^+$, $AL^{3+}$, $Y^{3+}$, $Ce^{3+}$, $Nd^{3+}$, $La^{3+}$, $C^{4+}$, and voids. Examples of $BO_4$ include $PO_4^{3-}$, $CO_3^{2-}$, $CrO_4^{3-}$, $AsO_4^{3-}$, $VO_4^{3-}$, $UO_4^{3-}$, $SO_4^{2-}$, $SiO_4^{4-}$, $GeO_4^{4-}$, and voids. Examples of C include $OH^-$, $OD^-$, $F^-$, $Br^-$, $BO^{2-}$, $CO_3^{2-}$, $O^{2-}$, and voids.

$A_{10}(BO_4)_6C_2$ is the basic structural formula of apatite, and $Ca_{10}(PO_4)_6(OH)_2$ is the basic structural formula of calcium phosphate apatite, though the apatite of the present invention is not limited by these basic structural formulas. In the case of, for example, calcium phosphate apatite, Ca-deficient apatite $Ca_{10-x}(HPO_4)_x(PO_4)_{6-x}(OH)_{2-x}$, carbonate apatite, substituted apatite, and the like are known, and all of them are included in the apatite of the present invention.

The tricalcium phosphate according to the present invention is a calcium phosphate compound comprising $Ca_3(PO_4)_2$ as typical composition and includes a compound in which a portion of calcium is substituted by a different metal ion such as sodium. The tricalcium phosphate includes α'-tricalcium phosphate and α-tricalcium phosphate with a high-temperature stable phase, and β tricalcium phosphate with a low-temperature stable phase. In the present invention, the α'-tricalcium phosphate and the α-tricalcium phosphate are collectively referred to as α-tricalcium phosphate.

The α-tricalcium phosphate and the β-tricalcium phosphate, albeit having the same composition, largely differ in solubility and totally differ in in vivo behavior. Since the β-tricalcium phosphate has small solubility and is clinically applied as a bone replacement material, the β-tricalcium phosphate is generally more preferred than the α-tricalcium phosphate. On the other hand, the α-tricalcium phosphate has large solubility and is used as a bioactive cement component or the like. However, in the case of a bone defect that is not large or in the case of a porous material, the α-tricalcium phosphate may be more preferably used as a core section than the β-tricalcium phosphate.

The octacalcium phosphate according to the present invention is calcium phosphate comprising $Ca_8H_2(PO_4)_6 \cdot 5H_2O$ as typical composition.

The calcium carbonate according to the present invention is a calcium component comprising $CaCO_3$ as basic composition. A compound in which a portion of Ca is substituted by a different element such as Mg is also included in the calcium carbonate of the present invention.

The calcium sulfate according to the present invention is a calcium component comprising $CaSO_4$ as basic composition, and its hemihydrate and dihydrate are also known. These hydrates are also included in the calcium sulfate of the present invention.

The calcium-containing glass according to the present invention is one of a calcium component and is glass or glass ceramic comprising calcium. By melting and quenching a glass component comprising calcium, the calcium-containing glass can be produced by a method known in the art. Calcium-containing crystallized glass obtained by pulverizing, calcining, and crystallizing the calcium-containing glass is also included in the calcium-containing glass of the present invention. Examples thereof can include $Na_2O$—$CaO$—$SiO_2$—$P_2O_5$ glass called Bioglass (Registered trademark) (typical composition: 24.5% by mass of $Na_2O$, 24.5% by mass of CaO, 45% by mass of $SiO_2$, and 6% by mass of $P_2O_5$), and crystallized glass called Cerabone (Registered trademark) A-W (typical composition: 4.6% by mass of MgO, 44.7% by mass of CaO, 34.0% by mass of $SiO_2$, 16.2% by mass of $P_2O_5$, and 0.5% by mass of $CaF_2$). Such calcium-containing glass can be produced by a method known in the art.

The polymer material according to the present invention refers to an organic material having a molecular weight exceeding 10000. Specific examples of the polymer material can include: biopolymers such as collagen, gelatin, chitin, and chitosan; absorbable polymers such as polylactic acid, polyglycolic acid, poly(lactic-co-glycolic acid), and polycaprolactone; and polyether ether ketone (PEEK), polyether ketone (PEK), polyether ether ketone ketone (PEEKK), polyether ketone ester, polyimide, polysulfone, polyethylene, polypropylene, and polyethylene terephthalate. These polymer materials may be used alone or in combination of two or more thereof. Particularly, the polymer material can be mixed with the calcium compound described above or the like to produce a medical use honeycomb structure having flexibility. Specifically, in the case of imparting flexibility to the medical use honeycomb structure, the polymer material is allowed to exist in composition without performing a high-heat treatment such as a debindering treatment mentioned later.

<Method for Producing a Honeycomb Structure>

The method for producing the medical use honeycomb structure of the present invention comprises: an outer-walled structure preparation step of extruding a material through a die for forming honeycomb structure to prepare a honeycomb structure having an outer peripheral side wall; and an outer peripheral section processing step of removing the outer peripheral side wall of the honeycomb structure having an outer peripheral side wall to form through-hole grooves and through-hole inlets in an outer peripheral section, and preferably comprises a debindering step. The method may further comprise other steps such as a calcination step. The debindering step and the calcination step may be simultaneously performed.

Specifically, in order to produce the medical use honeycomb structure of the present invention made of hydroxyapatite, for example, a hydroxyapatite powder is first mixed with an organic binder, and the mixture is extrusion-molded by a method disclosed in Japanese Patent No. 3405536, Japanese Patent Laid-Open Publication No. 10-59784, etc. to prepare a honeycomb structure having an outer peripheral side wall as shown in FIG. 1 and comprising hydroxyapatite and the organic binder in composition (outer-walled structure preparation step). Next, at least a portion of the outer peripheral side wall of the honeycomb structure having an outer peripheral side wall is removed by grinding, cutting, or the like and processed to form through-hole grooves and through-hole inlets in the outer peripheral section (outer peripheral section processing step). The removal of the outer peripheral side wall may be performed after the debindering step and is generally performed before the debindering step because of favorable processability. In this context, the debindering refers to the removal of the organic binder. The debindering refers to, for example, the removal of the organic binder from a structure having a honeycomb structure prepared from a hydroxyapatite powder and the organic binder. The debindering can employ a conventionally performed common method and can be attained, for example, by heating and incinerating the organic binder. After the debindering step, calcination may be performed, if necessary. Through these steps, the medical use honeycomb structure of the present invention made of hydroxyapatite can be produced.

The organic binder is used for imparting viscosity necessary for extrusion to ceramic powder particles. An organic binder known in the art, such as a wax binder or an acrylic binder, can be used without limitations.

The production of a honeycomb structure comprising only ceramic in composition requires debindering, whereas the production of a honeycomb structure made of ceramic and a polymer with a priority given to flexibility does not require the debindering step.

A hydroxyapatite honeycomb structure is stable even at a high temperature and is sintered by calcination at a high temperature of 800° C. to 1300° C. without being decomposed. Therefore, it is easy to produce the honeycomb structure.

On the other hand, a carbonate apatite honeycomb structure excellent in cell adhesiveness or tissue adhesiveness undergoes thermal decomposition or reduces its cell adhesiveness or tissue adhesiveness by high-temperature calcination. Therefore, its effective production method is, for example, a method comprising producing honeycomb structures (precursors) differing in composition, and performing compositional conversion to carbonate apatite through dissolution-precipitation-type compositional conversion reaction while maintaining the macromorphology of the honeycomb structures.

A calcium carbonate honeycomb structure, a calcium sulfate honeycomb structure, an α-tricalcium phosphate honeycomb structure, and the like are effective as the precursors differing in composition of the carbonate apatite honeycomb structure from the viewpoint of solubility. Among them, a calcium carbonate honeycomb is particularly useful as a precursor because only carbonate apatite is present as a stable phase as compared with calcium carbonate, when immersed in an aqueous phosphate solution.

However, calcium carbonate is poorly sinterable and is thermally decomposed at a high temperature. Therefore, a method using calcium hydroxide is useful.

Specifically, preferred is a method comprising: an outer-walled structure preparation step of extruding a mixture of calcium hydroxide mixed with an organic binder through a die for forming a honeycomb structure to prepare a honeycomb structure having an outer peripheral side wall; a debindering step of debindering the honeycomb structure; a carbonation step of performing a carbonation treatment of the honeycomb structure simultaneously with or subsequently to the debindering step; and an apatite preparation step of adding an aqueous phosphate solution to the honeycomb structure that has undergone the carbonation step, wherein the method comprises, at any stage after the outer-walled structure preparation step, an outer peripheral section processing step of removing at least a portion of the outer peripheral side wall of the honeycomb structure having an outer peripheral side wall to form through-hole grooves and through-hole inlets in an outer peripheral section. The outer peripheral section processing step may be performed at any stage before or after the debindering step, before or after the carbonation step, and before or after the apatite preparation step.

For carbonating the honeycomb structure during debindering, it is preferred to perform the debindering under conditions that carbon dioxide and oxygen coexist with each other when the honeycomb structure is heated. Oxygen is essential for debindering, i.e., incinerating the binder. Theoretically, the debindering is attained in the presence of oxygen, but is less likely to occur if the partial pressure of oxygen is small. Therefore, the volume percentage of oxygen in an environment where the honeycomb structure is debindered is preferably 10% or more, more preferably 20% or more, further preferably 30% or more.

On the other hand, the carbonation of calcium hydroxide requires carbon dioxide. The organic binder (polymer material) contains carbon, and the debindering of the organic binder generates carbon dioxide. Therefore, it is not necessarily required to supply carbon dioxide. However, carbon dioxide is not present after the debindering, and in such an environment, calcium carbonate is susceptible to thermal decomposition. Hence, the volume percentage of carbon dioxide in an environment where the honeycomb structure is debindered is preferably 10% or more, more preferably 20% or more, further preferably 30% or more.

The debindering temperature differs depending on the volume percentages of oxygen and carbon dioxide in an environment where the honeycomb is debindered, the degree of whiteness required for the calcium carbonate honeycomb structure to be produced, etc. and is preferably 400° C. or higher and 900° C. or lower, more preferably 450° C. or higher and 800° C. or lower, further preferably 500° C. or higher and 700° C. or lower.

Although the production of a calcium carbonate honeycomb by a carbonation treatment simultaneously with debindering is economical because of a fewer number of steps, the carbonation may be performed after debindering. High-temperature debindering is performed using only oxygen when the simultaneous supply of oxygen and carbon dioxide is difficult, or performed in the atmosphere when even the supply of oxygen is difficult. In this approach, calcium carbonate or calcium hydroxide, or both are thermally decomposed to form calcium oxide. Calcium oxide present in the honeycomb structure is responsible for digestion and distorts the shape of the honeycomb structure without keeping the form upon immersing in water or weakens mechanical strength. Hence, when calcium oxide is formed, a carbonation treatment is performed again. The carbonation treatment is performed by the contact of the honeycomb structure with carbon dioxide. In the case of a dry process, the honeycomb structure is contacted with carbon dioxide at a temperature of 920° C. or lower which thermally decomposes calcium carbonate. In the case of a wet process, the honeycomb structure is contacted with carbon dioxide at a humidity of 50% or higher.

Next, the produced calcium carbonate honeycomb is immersed in an aqueous phosphate solution so that the composition is converted to carbonate apatite through dissolution-precipitation-type compositional conversion reaction while the honeycomb structure is maintained to produce a carbonate apatite honeycomb structure. Although the immersing treatment is preferred, a continuous spraying treatment or the like may be performed.

A production method for producing a carbonate apatite honeycomb structure by using a calcium sulfate honeycomb structure as a precursor is also useful. Since calcium sulfate is thermally stable, the carbonate apatite honeycomb structure can be produced by an approach similar to the method for producing a hydroxyapatite honeycomb structure.

Specifically, an exemplary method comprises: an outer-walled structure preparation step of extruding a mixture of calcium sulfate mixed with an organic binder through a die for forming structure formation to prepare a honeycomb structure having an outer peripheral side wall; a debindering step of debindering the honeycomb structure; and an apatite preparation step of adding an aqueous solution containing a carbonate and a phosphate or sequentially adding an aqueous solution containing a carbonate and an aqueous solution containing a phosphate to the honeycomb structure that has undergone the debindering step, wherein the method comprises, at any stage after the outer-walled structure preparation step, an outer peripheral section processing step of removing at least a portion of the outer peripheral side wall of the honeycomb structure having an outer peripheral side wall to form through-hole grooves and through-hole inlets in an outer peripheral section. The debindering step can be performed before or after the outer peripheral section processing step. The outer peripheral section processing step may be performed at any stage before or after the debindering step and before or after the apatite preparation step.

Specifically, a calcium sulfate powder is mixed with an organic binder, and the mixture is extrusion-molded by, for example, a method disclosed in Japanese Patent No. 3405536 or Japanese Patent Laid-Open Publication No. 10-59784 to prepare a honeycomb structure having an outer peripheral side wall as shown in FIG. 1 and comprising calcium sulfate and the organic binder in composition (outer-walled structure preparation step).

Next, the binder is debindered, i.e., burning and removed, through a debindering step known in the art.

This calcium sulfate honeycomb structure is immersed in, for example, an aqueous solution containing both a phosphate and a carbonate so that the composition is converted to carbonate apatite through dissolution-precipitation-type compositional conversion reaction while the honeycomb structure is maintained to produce a carbonate apatite honeycomb structure. Although this production method is convenient, a sulfuric acid group may be detected in the composition of the carbonate apatite honeycomb structure. This is presumably because, since the honeycomb structure exhibits a cell structure, the diffusion of the solution in the interior of the cell structure is limited.

Hence, a production method may be more preferred which comprises: immersing the calcium sulfate honeycomb structure in a solution containing a carbonate so that the composition is converted to calcium carbonate through dissolution-precipitation-type compositional conversion reaction while maintaining the honeycomb structure to produce a calcium carbonate honeycomb structure; and then immersing the calcium carbonate honeycomb structure in a solution containing a phosphate so that the composition is converted to carbonate apatite through dissolution-precipitation-type compositional conversion reaction while maintaining the honeycomb structure to produce a carbonate apatite honeycomb structure.

<Method for Producing Honeycomb Structure Crushed Product>

The method for producing the medical use honeycomb structure crushed product of the present invention comprises: an outer-walled structure preparation step of extruding a material through a die for honeycomb structure formation to prepare a honeycomb structure having an outer peripheral side wall; an outer peripheral section processing step of removing at least a portion of the outer peripheral side wall of the honeycomb structure having an outer peripheral side wall to form through-hole grooves and through-hole inlets in an outer peripheral section; and a crushing step of crushing the honeycomb structure formed with the through-hole grooves and the through-hole inlets into a size of $10^{-12}$ m$^3$ or larger and smaller than $10^{-8}$ m$^3$, and may comprise a debindering step, a calcination step, and the like.

The crushing can be performed after the extrusion step, after the debindering step, or after the calcination step. In the case of a ceramic honeycomb structure, however, a honeycomb structure produced after the debindering step and after the calcination step is fragile. Thus, the desired granules may be difficult to produce by crushing, or the yield may be low.

Hence, it is preferred to perform the crushing before the debindering step. The crushing can be performed using a crusher or a pulverizer known in the art, such as a cutting mill. After the crushing, the granules are classified through a sieve or the like to produce a honeycomb structure crushed product having the desired size.

[Second Medical Use Honeycomb Structure of the Present Invention]

The second medical use honeycomb structure of the present invention is a medical use honeycomb structure comprising a plurality of through-holes extending in one direction, wherein the medical use honeycomb structure is constituted by a composition containing carbonate apatite. Specifically, the second medical use honeycomb structure of the present invention includes both the medical use honeycomb structures described above from which the outer peripheral side wall has been removed (e.g., the structure shown in FIG. 2) or is not removed (e.g., the structure shown in FIG. 1). The description about the medical use honeycomb structure described above can be applied directly to the description of each configuration.

The crushed product of the second medical use honeycomb structure of the present invention is obtained by crushing the second medical use honeycomb structure. The description about the medical use honeycomb structure crushed product described above can be applied directly to the description of each configuration.

Examples of the method for producing the second medical use honeycomb structure of the present invention as described above can include the above-described method itself for producing the medical use honeycomb structure of the present invention comprising carbonate apatite in composition (the peripheral side wall removed) and method without the outer peripheral section processing step (with the outer peripheral side wall).

Specific examples of the method for producing the second medical use honeycomb structure can include a method comprising: an outer-walled structure preparation step of extruding a mixture of calcium hydroxide mixed with an organic binder through a die for forming honeycomb structure to prepare a honeycomb structure having an outer peripheral side wall; a debindering step of debindering the honeycomb structure; a carbonation step of performing a carbonation treatment of the honeycomb structure simultaneously with or subsequently to the debindering step; and an apatite preparation step of adding an aqueous phosphate solution to the honeycomb structure that has undergone the carbonation step, and a method comprising: an outer-walled structure preparation step of extruding a mixture of calcium sulfate mixed with an organic binder through a die for forming honeycomb structure to prepare a honeycomb structure having an outer peripheral side wall; a debindering step of debindering the honeycomb structure; and an apatite preparation step of adding an aqueous solution containing a carbonate and a phosphate or sequentially adding an aqueous solution containing a carbonate and an aqueous solution containing a phosphate to the honeycomb structure that has undergone the debindering step.

[Working Effect of Medical Use Honeycomb Structure of the Present Invention]

The medical use honeycomb structure of the present invention satisfies demands desired of a medical use material, namely: (1) having excellent adhesiveness or binding of a cell or a tissue to a material surface; (2) can regenerate/reconstruct an oriented tissue; (3) having excellent mechanical strength; (4) when used as a tissue replacement material, quickly replacing a desired tissue; and (5) being able to be produced at a low cost. The mechanism underlying the medical use honeycomb structure of the present invention that satisfies these demands is probably as follows.

<(1) Excellent Adhesiveness or Binding of Cell or Tissue to Material Surface>

A medical use material is often required to bind to surrounding tissues when implanted in vivo. A surface constituted by the ends of the through-holes of the honeycomb structure (surface C of FIG. 1) has an open structure and is therefore not problematic. In general, an outer peripheral side surface (surface A of FIG. 1) has an outer peripheral side wall and is thus unlikely to bind to surrounding tissues. In the honeycomb structure of the present invention, the surface A is provided with through-hole grooves, and through-hole inlets which are opened to the through-hole direction. Hence, for example, bone tissues penetrate to the interior of the honeycomb structure from these sites and the honeycomb structure binds strongly to the surrounding bones.

In the case of containing carbonate apatite in the composition of the honeycomb structure, carbonate apatite is absorbed by osteoclasts and the like. Therefore, even when the original carbonate apatite honeycomb structure has an outer peripheral side wall, osteoclasts absorb the surface A. As a result, through-hole inlets which are opened in the through-hole direction are formed. For example, bone tissues penetrate to the interior of the honeycomb structure from these sites so that the honeycomb structure binds strongly to the surrounding bones. Specifically, in the case of containing carbonate apatite, it is not necessary to have through-hole grooves and through-hole inlets in the outer peripheral section.

The medical use honeycomb structure having through-hole grooves and through-hole inlets in an outer peripheral section and comprising carbonate apatite in composition is very superior in binding to surrounding bones and the like.

<(2) Regeneration/Reconstruction of Oriented Tissue>

The formation of oriented tissues is important from the viewpoint of the functionality of regenerated/reconstructed tissues. As reported in Non Patent Literature 1, tissues such as bones are variously oriented depending on sites. However, as pointed out in Non Patent Literatures 2 and 3, etc., regenerated bones are poorly orientational and poorly functional. Therefore, it has been pointed out that the induction of orientation is necessary.

The interior of the honeycomb structure of the present invention is an oriented interconnected porous material, and the induction of tissue orientation can be ideally performed because tissues are regenerated/reconstructed along the through-hole surfaces of the honeycomb structure. Furthermore, through-hole grooves, and through-hole inlets which are opened to the through-hole direction are also present in the outer peripheral section of the honeycomb structure of the present invention. Therefore, the induction of tissue orientation can be ideally performed because tissues are regenerated/reconstructed along these through-hole grooves and through-hole inlets.

In the case of containing carbonate apatite in the composition of the honeycomb structure, carbonate apatite is absorbed by osteoclasts and the like. Therefore, even when the original carbonate apatite honeycomb structure has an outer peripheral side wall, osteoclasts absorb the surface A. As a result, through-hole inlets which are opened to the through-hole direction are formed, and the induction of tissue orientation can be ideally performed. Specifically, in the case of containing carbonate apatite, it is not necessary to have through-hole grooves and through-hole inlets in the outer peripheral section.

The medical use honeycomb structure having through-hole grooves and through-hole inlets in an outer peripheral section and comprising carbonate apatite in composition is a honeycomb structure very superior in the formation of orientational tissues in an outer peripheral side surface.

<(3) Excellent Mechanical Strength>

The functioning of a medical use material at an implantation site without being destroyed is an essential requirement. The medical use honeycomb structure of the present invention has a honeycomb structure and is superior in mechanical strength as compared to other porous materials, and therefore satisfies this demand. The mechanical strength of the honeycomb structure is generally evaluated by measuring compressive strength or the like in the cell direction and in a direction perpendicular to cells. Mechanical strength equal to or greater than that of other porous materials having the same porosity thereas is exhibited by being a honeycomb structure.

<(4) when Used as Tissue Replacement Material, Quickly Replacing Desired Tissue>

A medical use material is replaced with tissues depending on the composition of the material. From this viewpoint, carbonate apatite, tricalcium phosphate, calcium sulfate, and calcium carbonate are excellent materials. Among them, carbonate apatite and tricalcium phosphate are much better materials, and carbonate apatite is a far much better material. The material is replaced with tissues by cells. For example, in the case of carbonate apatite, the material is replaced with tissues under a mechanism similar to bone remodeling in which osteoclasts resorb the material while osteoblasts form bones. Hence, the composition is not only the factor, and it is required that cells should be able to penetrate to the interior of the material or that a specific surface area should be large. In this respect, the medical use honeycomb structure of the present invention can employ the ideal material as described above. Furthermore, cells can penetrate to the interior of the interconnected cells, and the specific surface area is very large.

<(5) Able to be Produced at Low Cost>

The honeycomb structure of the present invention can be produced by a very convenient production method of, for example, merely extrusion-molding a material through a die for forming honeycomb and removing an outer peripheral side wall, and, if necessary, debindering the honeycomb structure and immersing the honeycomb structure in an aqueous solution. Therefore, the medical use honeycomb structure of the present invention can be produced at a low cost.

EXAMPLES

Hereinafter, the present invention will be described in detail with reference to Examples. However, the scope of the present invention is not limited by these Examples.

(Example 1) Honeycomb Structure (Block) Made of Calcium Carbonate

<Outer-Walled Structure Preparation Step>

Figure 6:
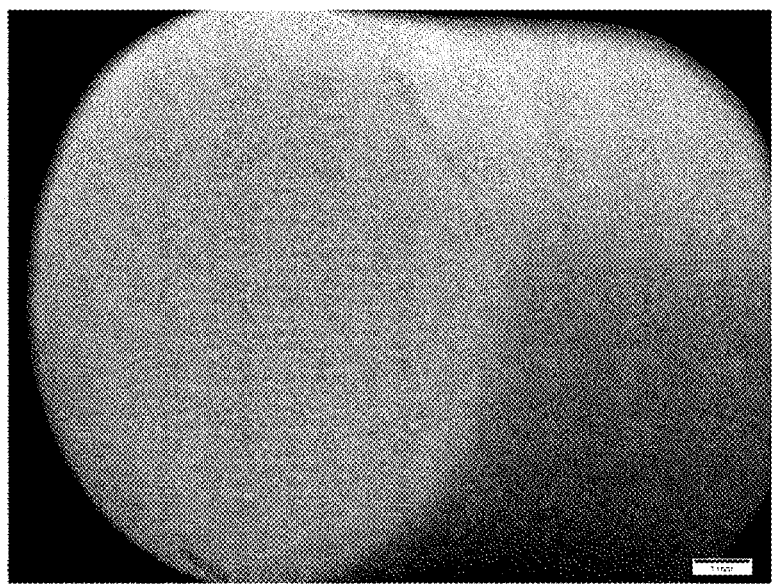

A calcium hydroxide powder manufactured by Nacalai Tesque, Inc. was pulverized into an average particle size of 1 μm using a jet mill, and the resulting calcium hydroxide was mixed with a wax binder manufactured by Nagamine Manufacturing Co., Ltd. at a weight ratio of 75:25. Then, a die for honeycomb molding was attached to Labo Plastomill manufactured by Toyo Seiki Co., Ltd., and extrusion molding was performed. As a result of the extrusion molding, a cylindrical binder-containing calcium hydroxide honeycomb structure having an outer peripheral side wall and comprising the mixture of calcium hydroxide and the binder in composition was prepared as an intermediate. The photograph of the prepared cylindrical binder-containing calcium hydroxide honeycomb structure having an outer peripheral side wall is shown in FIG. 6.

<Outer Peripheral Section Processing Step>

Figure 7:
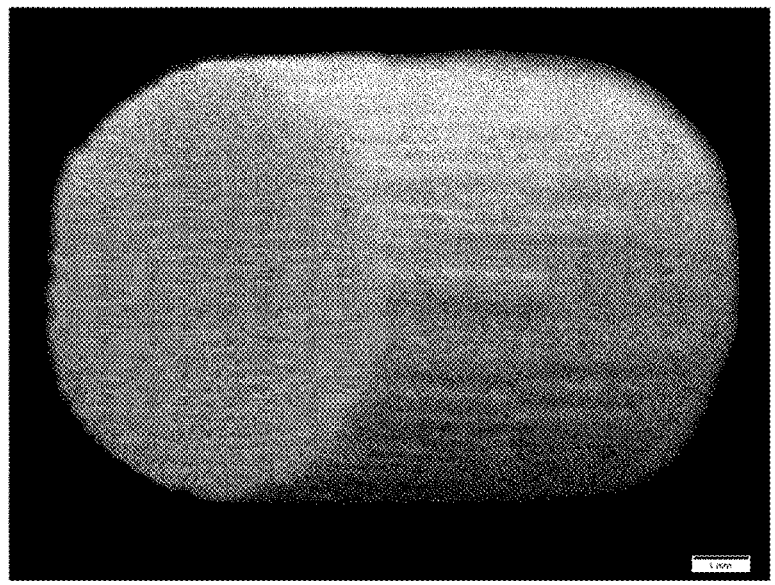

Next, the outer peripheral side wall of the cylindrical binder-containing calcium hydroxide honeycomb structure was removed with a power planer to form through-hole inlets, and through-hole grooves having a groove aspect ratio of 1.5 or more, continuous with the through-hole inlets, in the outer peripheral section. The photograph thereof is shown in FIG. 7.

<Debindering Step>

Next, the binder-containing calcium hydroxide honeycomb structure was debindered at 700° C. under a stream of oxygen containing 50% carbon dioxide. The composition of the honeycomb structure thus debindered was analyzed using a powder X-ray diffraction apparatus model D8 ADVANCE manufactured by Bruker Japan K.K. under conditions involving an output of 40 kV, 40 mA, and CuKα (λ=0.15418 nm) as an X-ray source and was confirmed to be a calcium carbonate.

Figure 8:
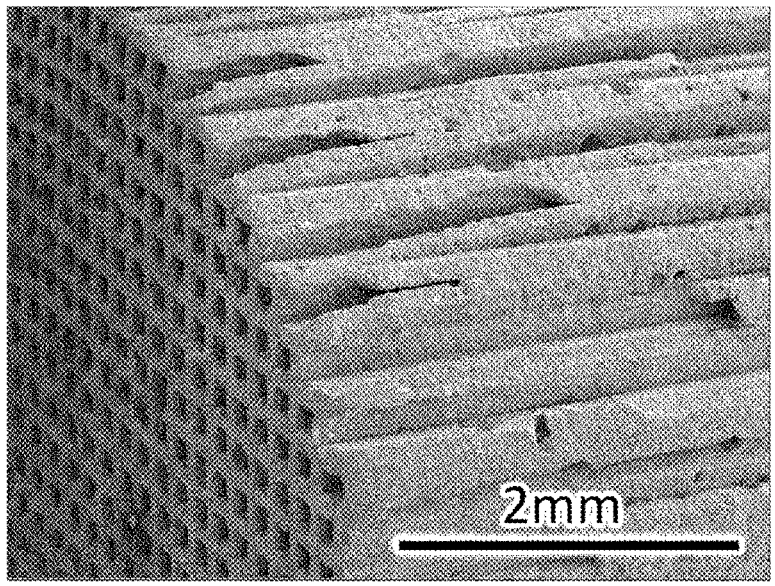

The electron microscope photograph (SEM photograph) of the honeycomb structure after the debindering step (honeycomb structure according to Example 1a) is shown in FIG. 8. It was confirmed that: a cylindrical calcium carbonate honeycomb structure block that retained cells even after the debindering and had no outer peripheral side wall was able to be produced; and through-hole inlets were formed in the outer peripheral section. Furthermore, it was confirmed that through-hole grooves were present, and that some through-hole grooves had a groove aspect ratio of 30 or more. Moreover, some through-hole inlets were confirmed to be present not only in the outermost layer but in the second outer layer. The rate of outer peripheral side wall removal (percentage of a concave-convex surface provided with the through-hole grooves and the through-hole inlets in the outer peripheral section) was 100%.

The through-hole diameter was 210 μm, the thickness of the partition wall was 150 μm, and the length of the through-hole was 30 mm. The volume of the produced honeycomb structure was $2\times10^{-6}$ m$^3$. The ratio of the through-hole diameter to the thickness of the partition wall was approximately 1.4, and the aspect ratio of the through-hole was approximately 140.

Next, in order to analyze the calcium carbonate honeycomb structure block for tissue compatibility, the orientation of regenerated/reconstructed tissues, and replaceability with bones, a calcium carbonate honeycomb structure (diameter: 7.2 mm, height: 4.5 mm) according to Example 1b produced in the same way as in Example 1a described above was implanted in a bone defect formed in the skull of a Japanese white rabbit, excised in a lump with surrounding tissues 1 month after the implantation, and histopathologically examined.

Figure 9A:
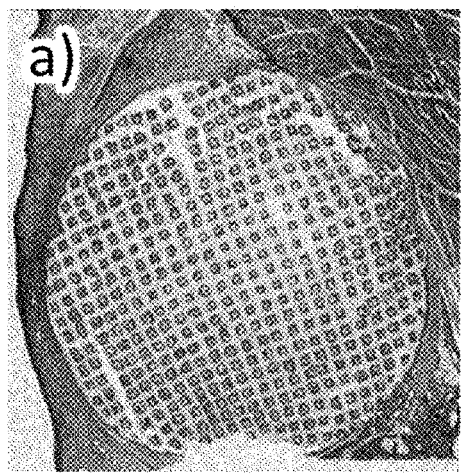
FIGS. 9(a) and 9(b) are low magnified images of a pathological tissue in histopathological examination using a honeycomb structure according to Example 1b.
Figure 9B:
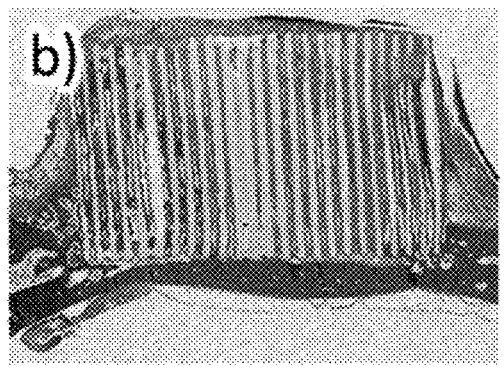

FIG. 9 shows a low magnified histopathological image of a pathological tissue stained with hematoxylin-eosin. FIG. 9(a) is an image of the honeycomb structure cut vertically to through-holes (cells), and FIG. 9(b) is an image of the honeycomb structure cut parallelly to through-holes (cells).

From the results of histopathological examination, it was found that: the calcium carbonate honeycomb structure block bound very favorably to surrounding tissues, including the outer peripheral side surface; and bone tissues completely penetrated to the interior of the calcium carbonate honeycomb structure block. It was also found that regenerated/reconstructed bone tissues were oriented in the long axis direction of the cells of the calcium carbonate honeycomb structure granules. Furthermore, osteoblasts and osteoclasts were observed on the surfaces of the calcium carbonate honeycomb structure granules. These results demonstrated that the calcium carbonate honeycomb structure block is replaced with bone tissues.

(Example 2) Honeycomb Structure Crushed Product (Granules) Made of Calcium Carbonate The cylindrical binder-containing calcium hydroxide honeycomb structure produced in Example 1 was crushed in a cutting mill (FRIGZ Medico Japan Co., Ltd., P-15) equipped with a 2.0 mm sieve. Then, the debindering step was performed under the same conditions as in Example 1.

Figure 10:
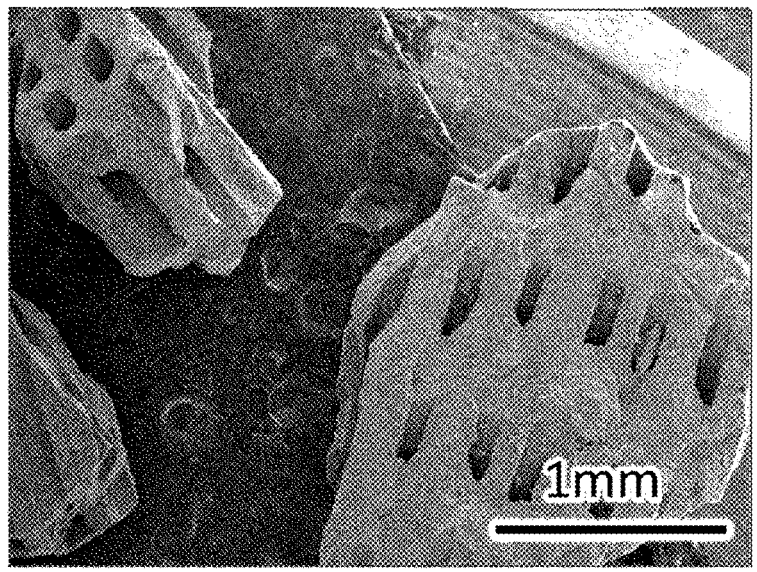
FIG. 10 is an electron microscope photograph (SEM photograph) of honeycomb structure granules according to Example 2.

The composition of the honeycomb structure granules after the debindering step was analyzed using a powder X-ray diffraction apparatus and was confirmed to be a calcium carbonate. The electron microscope photograph of the produced honeycomb structure granules is shown in FIG. 10. It was confirmed that cells were retained even after the debindering.

One example of the through-hole diameter was 210 μm, the thickness of the partition wall was 150 μm, and one example of the length of the through-hole was 2 mm. The volume of the produced honeycomb structure granules was $9\times10^{-10}$ m$^3$. The ratio of the through-hole diameter to the thickness of the partition wall was approximately 1.4. One example of the aspect ratio of the through-hole was approximately 10.

(Example 3) Honeycomb Structure (Block) with Different Cell Size Made of Calcium Carbonate A cylindrical calcium carbonate honeycomb structure having no outer peripheral side wall was produced by the same production method as in Example 1 except that a die for honeycomb molding different from that of Example 1 was used.

Figure 11:
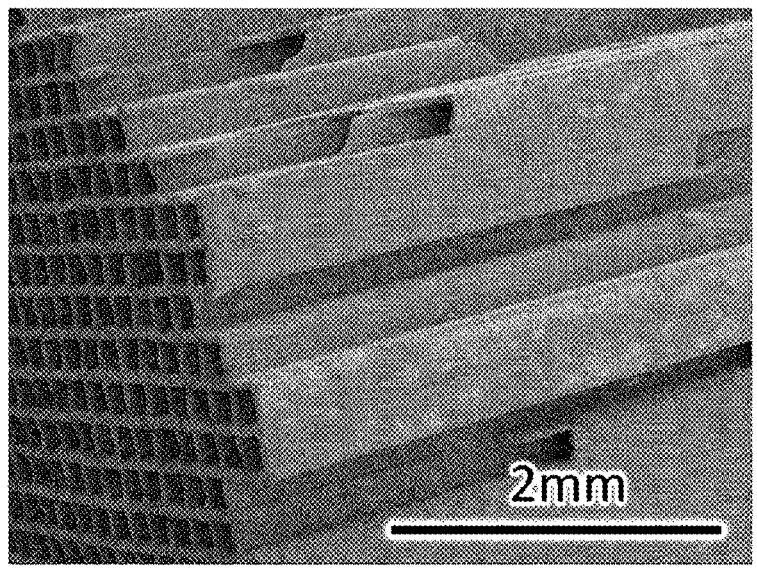
FIG. 11 is an electron microscope photograph (SEM photograph) of a honeycomb structure after a debindering step according to Example 3.

The composition of the honeycomb structure after the debindering step was confirmed to be calcium carbonate using a powder X-ray diffraction apparatus. The electron microscope photograph of the honeycomb structure after the debindering step is shown in FIG. 11. It was confirmed that: a cylindrical calcium carbonate honeycomb structure block that retains cells even after the debindering and having no outer peripheral side wall was able to be produced; and through-hole inlets were formed in the outer peripheral section. Furthermore, it was confirmed that through-hole grooves were present, and that some through-hole grooves had a groove aspect ratio of 30 or more. Moreover, some through-hole inlets were confirmed to be present not only in the outermost layer but in the second outer layer. The rate of outer peripheral side wall removal (percentage of a concave-convex surface provided with the through-hole grooves and the through-hole inlets in the outer peripheral section) was 100%.

The through-hole diameter was 170 μm, the thickness of the partition wall was 70 μm, and the length of the through-hole was 30 mm. The volume of the produced honeycomb structure was $1.5 \times 10^{-6}$ m$^3$. The ratio of the through-hole diameter to the thickness of the partition wall was approximately 2.4, and the aspect ratio of the through-hole was approximately 180.

(Example 4) Honeycomb Structure (Block) Made of Hydroxyapatite

The outer-walled structure preparation step and the outer peripheral section processing step were performed in the same way as in Example 1 except that hydroxyapatite manufactured by Taihei Chemical Industrial Co., Ltd. was used instead of the calcium hydroxide powder.

<Debindering Step>

Next, the binder-containing hydroxyapatite honeycomb structure was debindered in the atmosphere and calcined at 900° C. The composition of the honeycomb structure thus debindered was analyzed using a powder X-ray diffraction apparatus model D8 ADVANCE manufactured by Bruker Japan K.K. under conditions involving an output of 40 kV, 40 mA, and Kα ray of Cu ($\lambda$=0.15418 nm) as a characteristic X-ray source and was consequently found to be hydroxyapatite.

Figure 12:
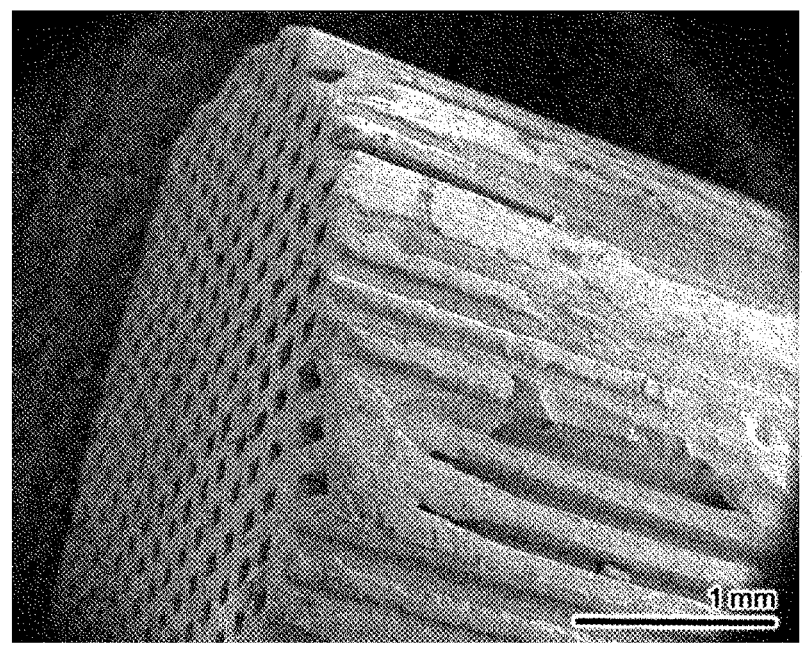
FIG. 12 is an electron microscope photograph (SEM photograph) of a honeycomb structure according to Example 4.

The electron microscope photograph (SEM photograph) of the honeycomb structure after the debindering step is shown in FIG. 12. It was confirmed that: a cylindrical hydroxyapatite honeycomb structure block that retains cells even after the debindering and having no outer peripheral side wall was able to be produced; and through-hole inlets were formed in the outer peripheral section. Furthermore, it was confirmed that through-hole grooves were present, and that some through-hole grooves had a groove aspect ratio of 30 or more. Moreover, some through-hole inlets were confirmed to be present not only in the outermost layer but in the second outer layer. The rate of outer peripheral side wall removal (percentage of a concave-convex surface provided with the through-hole grooves and the through-hole inlets in the outer peripheral section) was 100%.

The through-hole diameter was 210 μm, the thickness of the partition wall was 150 μm, and the length of the through-hole was 40 mm. The volume of the produced honeycomb structure was approximately $1.1 \times 10^{-6}$ m$^3$. The ratio of the through-hole diameter to the thickness of the partition wall was approximately 1.4, and the aspect ratio of the through-hole was approximately 190.

(Example 5) Honeycomb Structure Crushed Product (Granules) Made of Hydroxyapatite The cylindrical binder-containing hydroxyapatite honeycomb structure from which the outer peripheral section was removed, produced in Example 4 was pulverized, sifted, and classified into granules that passed through a 1000 μm sieve but did not pass through an 850 μm sieve. The obtained granules were subjected to the debindering step under the same conditions as in Example 4.

The composition of the honeycomb structure granules after the debindering step was analyzed using a powder X-ray diffraction apparatus and was consequently a hydroxyapatite. It was confirmed that cells were retained even after debindering. The through-hole diameter was 210 μm, the thickness of the partition wall was 150 μm, and one example of the length of the through-hole was 0.9 mm. One example of the volume of the produced honeycomb structure granules was approximately $5 \times 10^{-10}$ m$^3$. The ratio of the through-hole diameter to the thickness of the partition wall was approximately 1.4. One example of the aspect ratio of the through-hole was approximately 4.

(Example 6) Honeycomb Structure (Block) Made of Gypsum (Calcium Sulfate)

<Outer-Walled Structure Preparation Step>

Gypsum hemihydrate manufactured by Wako Pure Chemical Industries, Ltd. was heat-treated at 1000° C. to prepare anhydrous gypsum (anhydrous calcium sulfate). The prepared anhydrous gypsum was mixed with a wax binder manufactured by Nagamine Manufacturing Co., Ltd. at a weight ratio of 80:20. Then, a die for honeycomb molding was attached to Labo Plastomill manufactured by Toyo Seiki Co., Ltd., and extrusion molding was performed. As a result of the extrusion molding, a cylindrical binder-containing anhydrous gypsum honeycomb structure having an outer peripheral side wall and comprising the mixture of anhydrous gypsum and the binder in composition was prepared as an intermediate.

<Outer Wall Section Processing Step>

Next, the outer peripheral side wall of the cylindrical binder-containing anhydrous gypsum honeycomb structure was removed with a power planer to form through-hole inlets, and through-hole grooves having a groove aspect ratio of 1.5 or more, continuous with the through-hole inlets, in the outer peripheral section.

<Debindering Step>

Next, the binder-containing anhydrous gypsum honeycomb structure was debindered in the atmosphere and calcined at 1000° C. The composition of the honeycomb structure thus debindered was analyzed using a powder X-ray diffraction apparatus model D8 ADVANCE manufactured by Bruker Japan K.K. under conditions involving an output of 40 kV, 40 mA, and Kα ray of Cu ($\lambda$=0.15418 nm) as a characteristic X-ray source and was consequently found to be anhydrous gypsum.

Figure 13:
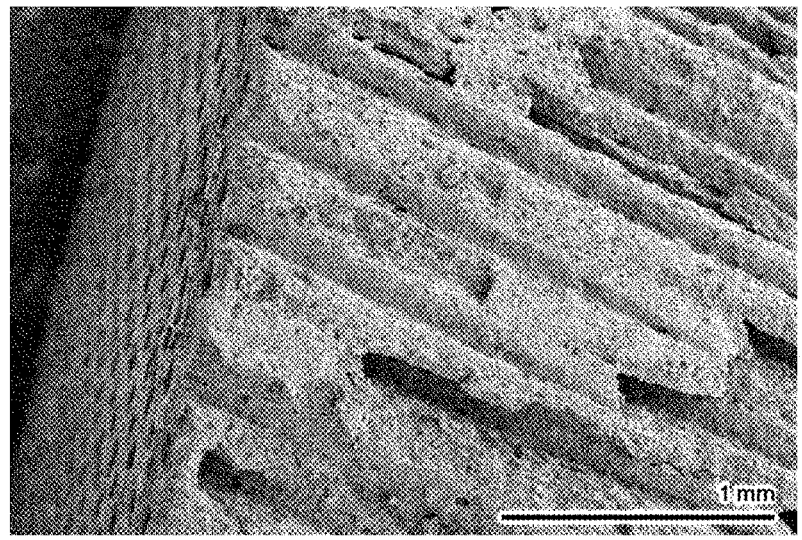
FIG. 13 is an electron microscope photograph (SEM photograph) of a honeycomb structure according to Example 6.

The electron microscope photograph (SEM photograph) of the honeycomb structure after the debindering step is shown in FIG. 13. It was confirmed that: a cylindrical anhydrous gypsum honeycomb structure block that retained cells even after the debindering and had no outer peripheral side wall was able to be produced; and through-hole inlets were formed in the outer peripheral section. Furthermore, it was confirmed that through-hole grooves were present, and that some through-hole grooves had a groove aspect ratio of 10 or more. Moreover, some through-hole inlets were confirmed to be present not only in the outermost layer but in the second outer layer. The rate of outer peripheral side wall removal (percentage of a concave-convex surface provided with the through-hole grooves and the through-hole inlets in the outer peripheral section) was 100%.

The through-hole diameter was 210 μm, the thickness of the partition wall was 150 μm, and the length of the through-hole was 21 mm. The volume of the produced honeycomb structure was approximately $6 \times 10^{-7}$ m$^3$. The ratio of the through-hole diameter to the thickness of the partition wall was approximately 1.4, and the aspect ratio of the through-hole was approximately 100.

(Example 7) Honeycomb Structure (Block) Made of β-Tricalcium Phosphate

<Outer-Walled Structure Preparation Step>

A β-tricalcium phosphate powder (β-TCP-A) manufactured by Taihei Chemical Industrial Co., Ltd. was mixed with a wax binder manufactured by Nagamine Manufacturing Co., Ltd. at a weight ratio of 75:25. Then, a die for honeycomb molding was attached to Labo Plastomill manufactured by Toyo Seiki Co., Ltd., and extrusion molding was performed. As a result of the extrusion molding, a cylindrical binder-containing β-tricalcium phosphate honeycomb structure having an outer peripheral side wall and comprising the mixture of β-tricalcium phosphate and the binder in composition was prepared as an intermediate.

<Outer Wall Section Processing Step>

Next, the outer peripheral side wall of the cylindrical binder-containing β-tricalcium phosphate honeycomb structure was removed with a power planer to form through-hole inlets, and through-hole grooves having a groove aspect ratio of 1.5 or more, continuous with the through-hole inlets, in the outer peripheral section.

<Debindering Step>

Next, the binder-containing β-tricalcium phosphate honeycomb structure was debindered in the atmosphere and calcined at 1050° C. The composition of the honeycomb structure thus debindered was analyzed using a powder X-ray diffraction apparatus model D8 ADVANCE manufactured by Bruker Japan K.K. under conditions involving an output of 40 kV, 40 mA, and Kα ray of Cu ($\lambda$=0.15418 nm) as a characteristic X-ray source and was consequently found to be a β-tricalcium phosphate.

Figure 14:
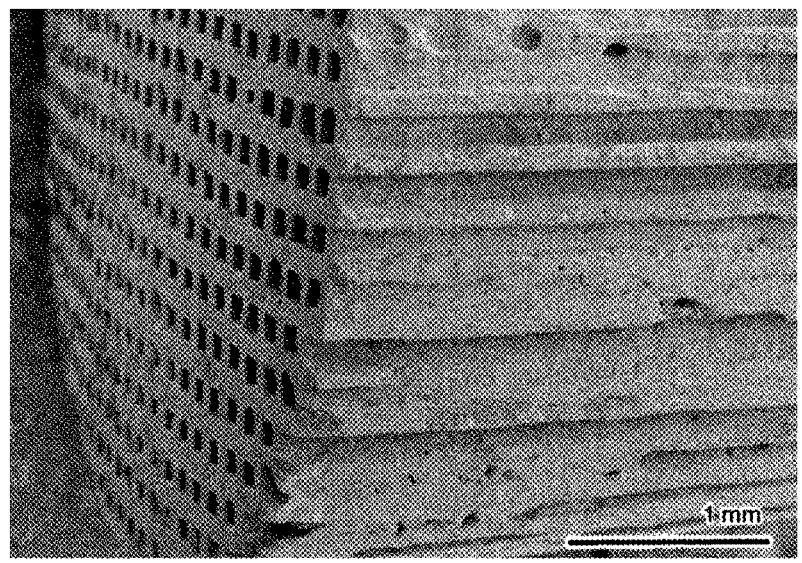
FIG. 14 is an electron microscope photograph (SEM photograph) of a honeycomb structure according to Example 7.

The electron microscope photograph (SEM photograph) of the honeycomb structure after the debindering step is shown in FIG. 14. It was confirmed that: a cylindrical β-tricalcium phosphate honeycomb structure block that retains cells even after the debindering and having no outer peripheral side wall was able to be produced; and through-hole inlets were formed in the outer peripheral section. Furthermore, it was confirmed that through-hole grooves were present, and that some through-hole grooves had a groove aspect ratio of 30 or more. Moreover, some through-hole inlets were confirmed to be present not only in the outermost layer but in the second outer layer. The rate of outer peripheral side wall removal (percentage of a concave-convex surface provided with the through-hole grooves and the through-hole inlets in the outer peripheral section) was 100%.

The through-hole diameter was 210 μm, the thickness of the partition wall was 150 μm, and the length of the through-hole was 18 mm. The volume of the produced honeycomb structure was approximately $5 \times 10^{-7}$ m$^3$. The ratio of the through-hole diameter to the thickness of the partition wall was approximately 1.4, and the aspect ratio of the through-hole was approximately 90.

(Example 8) Honeycomb Structure Crushed Product (Granules) Made of β-Tricalcium Phosphate The cylindrical binder-containing β-tricalcium phosphate honeycomb structure after the outer wall section processing step of Example 7 was pulverized using a cutter and a mortar. The pulverized binder-containing β-tricalcium phosphate honeycomb structure was sifted and classified into granules that passed through a 1000 μm sieve but did not pass through an 850 μm sieve. The obtained granules were subjected to the debindering step under the same conditions as in Example 7.

The composition of the honeycomb structure granules after the debindering step was analyzed using a powder X-ray diffraction apparatus and was consequently β-tricalcium phosphate. It was confirmed that cells were retained even after the debindering. The through-hole diameter was 210 μm, the thickness of the partition wall was 150 μm, and one example of the length of the through-hole was 0.9 mm. One example of the volume of the produced honeycomb structure granules was approximately $5 \times 10^{-10}$ m$^3$. The ratio of the through-hole diameter to the thickness of the partition wall was approximately 1.4. One example of the aspect ratio of the through-hole was approximately 4.

(Example 9) Honeycomb Structure (Block) Made of α-Tricalcium Phosphate

<Compositional Conversion Step>

The β-tricalcium phosphate honeycomb structure prepared in Example 7 was calcined at 1500° C. in the atmosphere to convert the composition to α-tricalcium phosphate. The composition of the honeycomb structure thus calcined was analyzed using a powder X-ray diffraction apparatus model D8 ADVANCE manufactured by Bruker Japan K.K. under conditions involving an output of 40 kV, 40 mA, and Kα ray of Cu ($\lambda$=0.15418 nm) as a characteristic X-ray source and was consequently found to be an α-tricalcium phosphate.

Figure 15:
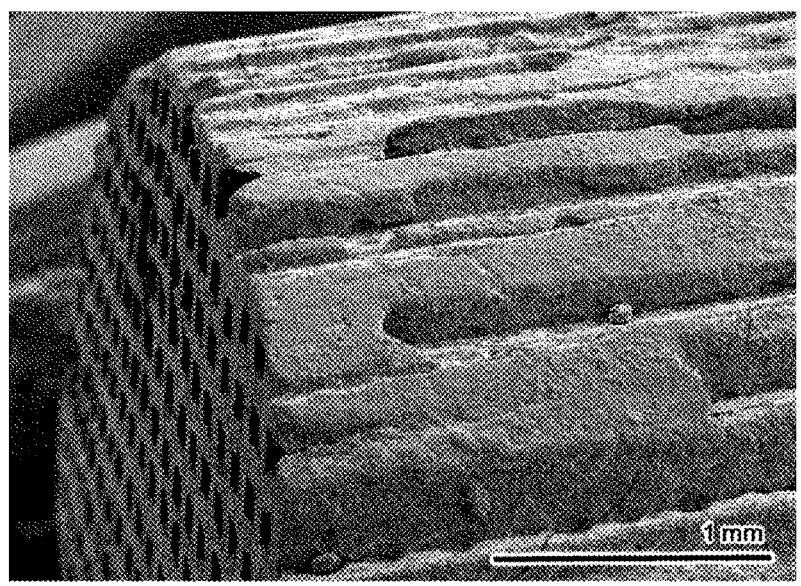
FIG. 15 is an electron microscope photograph (SEM photograph) of a honeycomb structure according to Example 9.

The electron microscope photograph (SEM photograph) of the honeycomb structure after the compositional conversion step is shown in FIG. 15. It was confirmed that: a cylindrical α-tricalcium phosphate honeycomb structure block that retains cells even after the compositional conversion step and having no outer peripheral side wall was able to be produced; and through-hole inlets were formed in the outer peripheral section. Furthermore, it was confirmed that through-hole grooves were present, and that some through-hole grooves had a groove aspect ratio of 30 or more. Moreover, some through-hole inlets were confirmed to be present not only in the outermost layer but in the second outer layer. The rate of outer peripheral side wall removal (percentage of a concave-convex surface provided with the through-hole grooves and the through-hole inlets in the outer peripheral section) was 100%.

The through-hole diameter was 210 μm, the thickness of the partition wall was 150 μm, and the length of the through-hole was 21 mm. The volume of the produced honeycomb structure was approximately $6 \times 10^{-7}$ m$^3$. The ratio of the through-hole diameter to the thickness of the partition wall was approximately 1.4, and the aspect ratio of the through-hole was approximately 100.

(Example 10) Honeycomb Structure Made of Polymer Material

<Outer-Walled Structure Preparation Step>

A die for honeycomb molding was attached to Labo Plastomill manufactured by Toyo Seiki Co., Ltd., and a polyolefin resin Tafmer MY-2 manufactured by Mitsui Chemicals, Inc. was extrusion-molded. As a result of the extrusion molding, a Tafmer honeycomb structure having a cylindrical outer peripheral side wall and comprising Tafmer in composition was prepared as an intermediate. The obtained Tafmer honeycomb structure had flexibility and was easily bendable by the hand.

<Outer Wall Section Processing Step>

Next, the outer peripheral side wall of the Tafmer honeycomb structure having a cylindrical outer peripheral side wall was removed with a cutter to form through-hole inlets, and through-hole grooves having a groove aspect ratio of 1.5 or more, continuous with the through-hole inlets, in the outer peripheral section.

Figure 16:
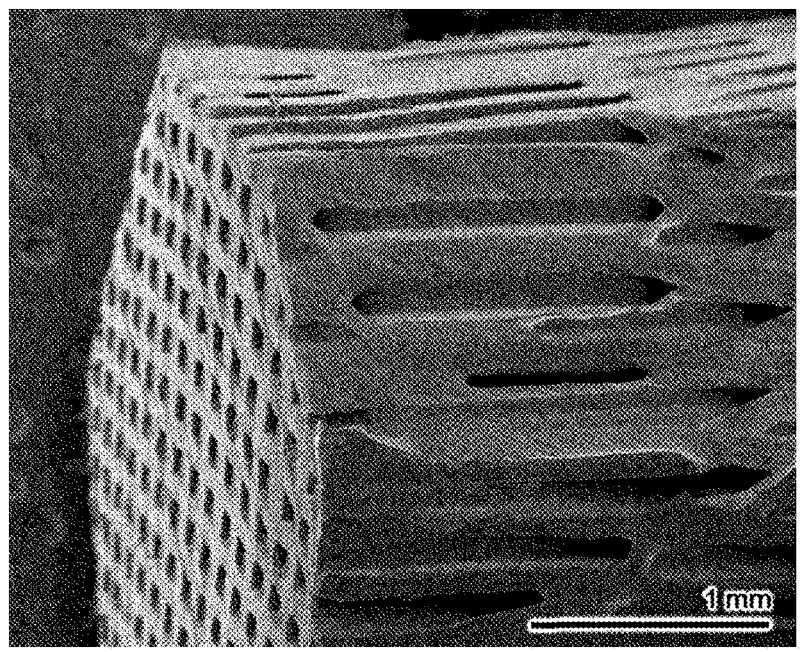
FIG. 16 is an electron microscope photograph (SEM photograph) of a honeycomb structure according to Example 10.

The electron microscope photograph (SEM photograph) of the honeycomb structure after the outer peripheral side wall removal is shown in FIG. 16. It was confirmed that: a Tafmer honeycomb structure block that retains cells even after the outer peripheral side wall removal and having no outer peripheral side wall was able to be produced; and through-hole inlets were formed in the outer peripheral section. Furthermore, it was confirmed that through-hole grooves were present, and that some through-hole grooves had a groove aspect ratio of 30 or more. Moreover, some through-hole inlets were confirmed to be present not only in the outermost layer but in the second outer layer. The rate of outer peripheral side wall removal (percentage of a concave-convex surface provided with the through-hole grooves and the through-hole inlets in the outer peripheral section) was 100%.

The through-hole diameter was 210 μm, the thickness of the partition wall was 100 μm, and the length of the through-hole was 30 mm. The volume of the produced honeycomb structure was approximately $2 \times 10^{-7}$ m$^3$. The ratio of the through-hole diameter to the thickness of the partition wall was approximately 2.1, and the aspect ratio of the through-hole was approximately 140.

(Example 11) Honeycomb Structure (Block) Made of Carbonate Apatite

The calcium carbonate honeycomb block produced in Example 1 was dipped in a 1 M aqueous disodium hydrogen phosphate solution of 80° C. for 7 days.

Figure 17:
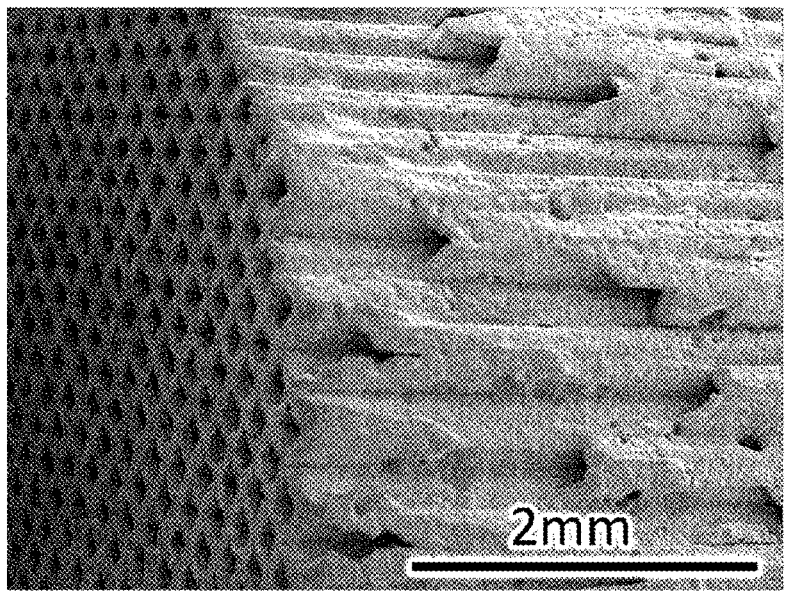

The composition of the produced honeycomb structure was analyzed using a powder X-ray diffraction apparatus and a Fourier transform infrared spectrometer and was consequently carbonate apatite. The carbonic acid group content was analyzed using a CHN elemental analysis apparatus and was consequently 10.8% by weight. The electron microscope photograph of the produced carbonate apatite honeycomb structure (honeycomb structure according to Example 11a) is shown in FIG. 17. It was confirmed that a carbonate apatite honeycomb structure block having no outer peripheral side wall was able to be produced. It was confirmed that: a cylindrical calcium carbonate honeycomb structure block that retains cells and having no outer peripheral side wall was able to be produced; and through-hole inlets were formed in the outer peripheral section. Furthermore, it was confirmed that through-hole grooves were present, and that some through-hole grooves had a groove aspect ratio of 30 or more. Moreover, some through-hole inlets were confirmed to be present not only in the outermost layer but in the second outer layer. The rate of outer peripheral side wall removal (percentage of a concave-convex surface provided with the through-hole grooves and the through-hole inlets in the outer peripheral section) was 100%.

The through-hole diameter was 210 μm, the thickness of the partition wall was 150 μm, and the length of the through-hole was 30 mm. The volume of the produced honeycomb structure was $2 \times 10^{-6}$ m$^3$. The ratio of the through-hole diameter to the thickness of the partition wall was approximately 1.4, and the aspect ratio of the through-hole was approximately 140.

The compressive strength in the penetrating direction (direction c of FIG. 1) of the produced carbonate apatite honeycomb block was 90 MPa, and the compressive strength thereof in a direction perpendicular to the penetrating direction (direction a of FIG. 1) was 2 MPa.

Next, in order to analyze the carbonate apatite honeycomb structure block for tissue compatibility, the orientation of regenerated/reconstructed tissues, and replaceability with bones, a carbonate apatite honeycomb (diameter: 6 mm, height: 5 mm) according to Example 11b produced in the same way as in Example 11a described above was implanted in a bone defect formed in the thigh bone of a Japanese white rabbit, excised in a lump with surrounding tissues 1 month after the implantation, and histopathologically examined.

Figure 18:
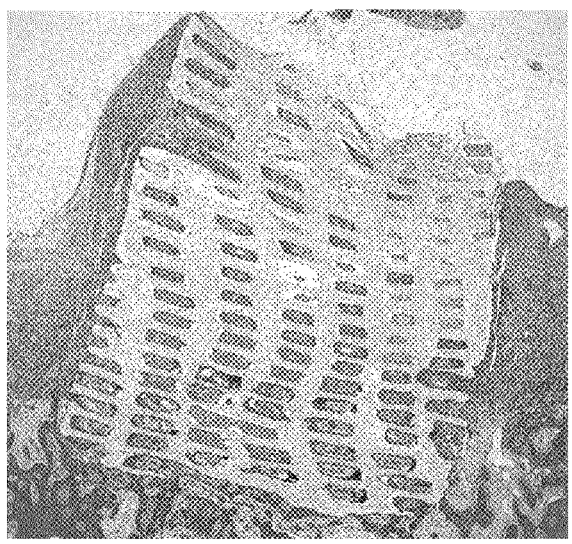
FIG. 18 is a low magnified image of a pathological tissue in histopathological examination using a honeycomb structure according to Example 11b.

FIG. 18 shows a low magnified image of a pathological tissue stained with hematoxylin-eosin. It was found that: the carbonate apatite honeycomb structure block bound very favorably to surrounding tissues, including the outer peripheral side surface; and bone tissues completely penetrated to the interior of the carbonate apatite honeycomb structure block.

Figure 19:
FIG. 19 is a highly magnified image of a pathological tissue of tissues that penetrated cells in a honeycomb structure mesial section from a through-hole inlet of an outer peripheral section, in histopathological examination using the honeycomb structure according to Example 11b.

FIG. 19 shows a highly magnified image of a pathological tissue of the tissues that penetrated cells in a honeycomb structure mesial section from the through-hole inlets of the outer peripheral section which opened in the through-hole direction. No inflammatory finding was observed. As seen therefrom, the formed bone tissues were highly oriented in the long axis direction of the cells of the carbonate apatite honeycomb structure block. Multinuclear osteoclasts and osteoblasts were observed on the surfaces of the oriented bones formed on the partition wall surfaces of the carbonate apatite honeycomb structure block, and bone cells were observed in the interior of the formed bones. This demonstrated that: bones formed in the interior of the honeycomb structure actively perform bone remodeling; and the carbonate apatite honeycomb structure block is therefore replaced with bone tissues. Vascular endothelial cells were observed in the interior of the carbonate apatite honeycomb cells, and erythrocytes were confirmed in the vascular endothelial cells. This demonstrated that vascular vessels are formed in the interior of the carbonate apatite honeycomb. Oxygen and nutrients are supplied to bones formed through vascularization, demonstrating that bones are regenerated at a very high level by the carbonate apatite honeycomb structure.

(Example 12) Honeycomb Structure Crushed Product (Granules) Made of Carbonate Apatite The calcium carbonate honeycomb structure granules produced in Example 2 were dipped in a 1 M aqueous disodium hydrogen phosphate solution of 80° C. for 7 days. The composition of the honeycomb structure granules was analyzed using a powder X-ray diffraction apparatus and a Fourier transform infrared spectrometer and was consequently carbonate apatite. The carbonic acid group content was analyzed using a CHN elemental analysis apparatus and was consequently 10.8% by weight.

Figure 20:
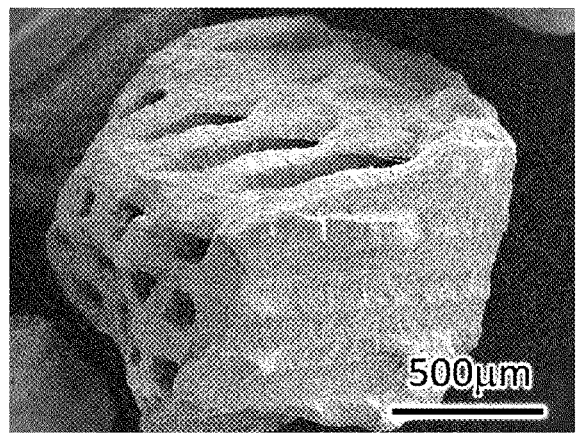
FIG. 20 is an electron microscope photograph (SEM photograph) of honeycomb structure granules according to Example 12.

The electron microscope photograph of the produced carbonate apatite honeycomb structure granules is shown in FIG. 20. The structure was basically retained even after compositional conversion.

The through-hole diameter was 210 μm, the thickness of the partition wall was 150 μm, and one example of the length of the through-hole was 1 mm. One example of the volume of the produced honeycomb structure granules was $8 \times 10^{-10}$ m$^3$. The ratio of the through-hole diameter to the thickness of the partition wall was approximately 1.4. The aspect ratio of the through-hole was approximately 5.

Next, in order to analyze the carbonate apatite honeycomb structure granules for tissue compatibility, the orientation of regenerated/reconstructed tissues, and replaceability with bones, the carbonate apatite honeycomb was implanted in a bone defect formed in the thigh bone of a Japanese white rabbit, excised in a lump with surrounding tissues 1 month after the implantation, and histopathologically examined.

Figure 21:
FIG. 21 is a low magnified image of a pathological tissue in histopathological examination using a honeycomb structure according to Example 12.

FIG. 21 shows a low magnified image of a pathological tissue stained with hematoxylin-eosin. It was found that: the carbonate apatite honeycomb structure granules bound very favorably to surrounding tissues; and bone tissues completely penetrated to the interior of the carbonate apatite honeycomb structure granules.

Figure 22:
FIG. 22 is a highly magnified image of a pathological tissue of tissues that penetrated cells in a honeycomb structure mesial section from a through-hole inlet of an outer peripheral section opened in the through-hole direction of the honeycomb structure according to Example 12.

FIG. 22 shows a highly magnified image of a pathological tissue of the tissues that penetrated cells in a honeycomb structure mesial section from the through-hole inlets of the outer peripheral section which are opened to the through-hole direction. As seen therefrom, the regenerated/reconstructed bone tissues were oriented in the long axis direction of the cells of the carbonate apatite honeycomb structure granules. Osteoclasts were observed on the surfaces of the carbonate apatite honeycomb structure granules. This demonstrated that the carbonate apatite honeycomb structure granules are replaced with bone tissues.

(Example 13) Carbonate Apatite Honeycomb Block Having Outer Peripheral Side Wall A calcium carbonate honeycomb structure having an outer peripheral side wall was produced as an intermediate in the same way as in Example 1 without processing the outer peripheral side wall, and dipped in a 1 M aqueous disodium hydrogen phosphate solution of 80° C. for 7 days.

The composition of the honeycomb structure block was analyzed using a powder X-ray diffraction apparatus and a Fourier transform infrared spectrometer and was consequently carbonate apatite. The carbonic acid group content was analyzed using a CHN elemental analysis apparatus and was consequently 10.5% by weight. The produced carbonate apatite honeycomb structure basically maintained the structure of the intermediate calcium carbonate honeycomb structure, confirming that a carbonate apatite honeycomb structure block having an outer peripheral side wall was able to be produced.

Next, in order to analyze the carbonate apatite honeycomb structure block for tissue compatibility, the orientation of regenerated/reconstructed tissues, and replaceability with bones, the carbonate apatite honeycomb was implanted in a bone defect formed in the thigh bone of a Japanese white rabbit, excised in a lump with surrounding tissues 1 month after the implantation, and histopathologically examined.

It was found that: the carbonate apatite honeycomb structure block bound very favorably to surrounding tissues, including the outer peripheral sidewall surface; and bone tissues completely penetrated the interior of the carbonate apatite honeycomb structure block. A portion of the outer peripheral side wall of the carbonate apatite honeycomb was absorbed, demonstrating that oriented bone tissues also penetrated the interior of the honeycomb structure from the outer peripheral side wall.

(Comparative Example 1) Hydroxyapatite Honeycomb Block Having Outer Peripheral Side Wall For the purpose of verifying the usefulness of the carbonate apatite honeycomb shown in Example 13, a hydroxyapatite honeycomb having the same structure as that of the carbonate apatite of Example 13 and comprising hydroxyapatite in composition was prepared.

A hydroxyapatite powder was pulverized into an average particle size of 1 µm using a jet mill, and the resulting hydroxyapatite powder was mixed with a wax binder at a weight ratio of 75:25. Then, a die for honeycomb molding was attached to Labo Plastomill, and extrusion molding was performed. As a result of the extrusion molding, a cylindrical binder-containing hydroxyapatite powder honeycomb structure having an outer peripheral side wall and comprising the mixture of the hydroxyapatite powder and the binder in composition was prepared as an intermediate.

Next, the binder-containing hydroxyapatite powder honeycomb structure was debindered at 700° C. in air and further calcined at 1200° C. for 6 hours.

The composition of the honeycomb structure thus calcined was analyzed using a powder X-ray diffraction apparatus model D8 ADVANCE manufactured by Bruker Japan K.K. and was consequently found to be a hydroxyapatite.

Next, in order to analyze the hydroxyapatite honeycomb structure block having an outer peripheral side wall for tissue compatibility, the orientation of regenerated/reconstructed tissues, and replaceability with bones, the hydroxyapatite honeycomb structure having an outer peripheral side wall was implanted in a bone defect formed in the thigh bone of a Japanese white rabbit, excised in a lump with surrounding tissues 1 month after the implantation, and histopathologically examined.

A surface constituted by the ends of the through-holes (surface C of FIG. 1) of the hydroxyapatite honeycomb structure having an outer peripheral side wall bound favorably with surrounding tissues, though the degree of this binding was poor as compared with the carbonate apatite honeycomb of Example 13. Also, the binding of the outer peripheral side wall surface to surrounding tissues was limited. In addition, the entry of bone tissues to the hydroxyapatite honeycomb structure was limited as compared with the penetration of bone tissues to the interior of the carbonate apatite honeycomb structure block. This demonstrated that the penetration of bones tissues to the cells of the carbonate apatite honeycomb structure is also excellent as compared with hydroxyapatite. A honeycomb structure other than the honeycomb structure comprising carbonate apatite was found to be problematic for the binding of the honeycomb structure to surrounding tissues, if having an outer peripheral side wall.

<Confirmation Test on Penetration of Bone to Through-Hole>

Next, the degree of penetration of bones to through-holes was compared between the carbonate apatite honeycomb and the hydroxyapatite honeycomb.

As shown in Example 13 and Comparative Example 1, the comparison between carbonate apatite and hydroxyapatite having an outer peripheral side wall demonstrated that the amount of bones penetrating from the surface constituted by the ends of the through-holes (surface C of FIG. 1) differs between the honeycombs even having the same pore size. Accordingly, the degree of penetration of bones from the surface C was confirmed as to the carbonate apatite honeycomb having an outer peripheral side wall and the hydroxyapatite honeycomb having an outer peripheral side wall. The results are shown in Table 1.

TABLE 1

| Through-hole diameter | carbonate apatite | Hydroxyapatite |
| --- | --- | --- |
| 70 μm | Bones entered from the entire surface C Vascularized | Bone entry from the surface C was very limited Not vascularized |
| 170 μm | Bones entered from the entire surface C Vascularized | Bone entry from the surface C was limited Not vascularized |
| 210 μm | Bones entered from the entire surface C Vascularized | Bone entry from the surface C was slightly limited Not vascularized |
| 280 μm | Bones entered from the entire surface C Vascularized | Bone entry from the surface C was observed, but was limited as compared with the carbonate apatite honeycomb Not vascularized |

It is generally known that the penetration of tissues to the interior of pores is less likely to take place as the diameter of the pores is smaller. For the continuous functioning of tissues that have penetrated the interior of pores, vascularization is essential. As shown in Table 1, the carbonate apatite honeycomb was found to be superior in the penetration of bones from the surface C to hydroxyapatite at least when the through-hole diameter is 280 μm or smaller. Particularly, in the case of the through-hole diameters of 70 μm and 170 μm, the penetration of bones to the interior of the honeycomb structure comprising hydroxyapatite in composition was very limited or limited, whereas the penetration of bones to the interior of the carbonate apatite honeycomb structure from the entire surface C was observed. Specifically, in the case of a through-hole diameter of 170 μm or smaller, marked different in effect from hydroxyapatite was seen.

In the case of hydroxyapatite, no vascularization was observed even for the maximum through-pore diameter of 280 μm at the stage of implantation week 4. By contrast, it was found that: bone tissues penetrated the carbonate apatite honeycomb even having the maximum through-pore diameter of 70 μm; and vascularization was observed in the bone tissues.

The mechanism is unknown under which the carbonate apatite honeycomb exerts markedly different functions from those of other honeycombs having distinctive composition and also exerts marked different functions from those of a carbonate apatite block or the like having no honeycomb structure. Synergistic effects probably occurred through the recognition of composition by cells such as macrophages and the formation of a microenvironment by the honeycomb structure.

Specifically, when a medical material is implanted in living tissues, the biomaterial is recognized as a foreign substance by macrophages to be phagocytized. As a result, the carbonate apatite honeycomb or the hydroxyapatite honeycomb is partially dissolved so that calcium ions or phosphoric acid ions are supplied to body fluids. The macrophages recognize the calcium ions or the phosphoric acid ions via Ca-sensing receptor (CaSR) or the like and are thus activated to release cytokines or growth factors. Carbonate apatite has the same composition as that of living bones and elutes calcium ions or phosphoric acid ions at the same ratio as that of living bones or has larger solubility than that of hydroxyapatite in an acidic environment in the course of phagocytosis by macrophages. Therefore, carbonate apatite probably causes a larger amount of cytokines or growth factors released by the activation of macrophages.

Meanwhile, when carbonate apatite retains no through-hole extending in one direction through a honeycomb structure, for example, is a dense body, cytokines or growth factors released by macrophages are diffused. Therefore, the activation of osteoblasts and the like is limited. Even when a porous material of carbonate apatite retains no through-hole extending in one direction, for example, is a foamy porous material, cytokines or growth factors released by macrophages are three-dimensionally diffused, albeit in a limited manner, as compared with the carbonate apatite surface of the dense body. Therefore, the localization of the cytokines or growth factors released by macrophages is still limited. On the other hand, the carbonate apatite honeycomb retains through-holes extending in one direction and probably localizes therein cytokines or growth factors released by macrophages. As a result, osteoblasts and the like are highly activated, probably forming bones, and vascular vessels essential for maintaining the functions of the formed bones.

INDUSTRIAL APPLICABILITY

The medical use honeycomb structure of the present invention satisfies demands desired of a medical use material, namely: (1) having excellent adhesiveness or binding of a cell or a tissue to a material surface; (2) can regenerate/reconstruct an oriented tissue; (3) having excellent mechanical strength; (4) when used as a tissue replacement material, quickly replacing a desired tissue; and (5) being able to be produced at a low cost, and is widely applicable in the medical field or fields related to medicine.

REFERENCE SIGNS LIST

10 Medical use honeycomb structure of the present invention
11 Through-hole
12 Partition wall
13 Outer peripheral side wall
14 Honeycomb structure having an outer peripheral side wall
15 Through-hole inlet
16 Through-hole groove

The invention claimed is:
1. A medical use honeycomb structure, comprising:
a plurality of through-holes extending in one direction, wherein
an outer peripheral section of the medical use honeycomb structure has a through-hole groove formed by scraping a side wall of a through-hole among the plurality of through-holes, and a through-hole inlet adjacent to the through-hole groove, wherein an inclined surface which is inclined with respect to a penetrating direction of the through-hole is formed in the outer peripheral section.

2. The medical use honeycomb structure according to claim 1, wherein a ratio of a length in a longitudinal direction to a length in a width direction of the through-hole groove is 1.5 or more.

3. The medical use honeycomb structure according to claim 1, wherein at least an outermost layer and a second outer layer in an inner side thereof are each provided with a respective through-hole groove and a respective through-hole inlet.

4. The medical use honeycomb structure according to claim 1, wherein a piercing hole which pierces the side wall of the through-hole is provided.

5. The medical use honeycomb structure according to claim 1, wherein a thickness of an outer peripheral side wall of the outer peripheral section is 300 μm or smaller.

6. The medical use honeycomb structure according to claim 1, wherein a ratio of a length in a longitudinal direction to a diameter of the through-hole is 3 or more.

7. The medical use honeycomb structure according to claim 1, wherein the medical use honeycomb structure is made of a composition containing at least one type selected from the group consisting of apatite, β-tricalcium phosphate, α-tricalcium phosphate and octacalcium phosphate.

8. The medical use honeycomb structure according to claim 1, wherein the medical use honeycomb structure is made of a composition containing carbonate apatite.

9. A crushed product of a medical use honeycomb structure according to claim 1.

10. The crushed product according to claim 9, wherein the crushed product has a size of $10^{-12}$ m$^3$ or larger and smaller than $10^{-8}$ m$^3$.

11. A method for producing the medical use honeycomb structure according to claim 1, the method comprising:
an outer-walled structure preparation process of extruding a material through a die for forming the honeycomb structure having an outer peripheral side wall; and
an outer peripheral section processing process of removing at least a portion of the outer peripheral side wall of the honeycomb structure to form the through-hole groove and the through-hole inlet in the outer peripheral section.

12. A method for producing a medical use honeycomb structure crushed product from the medical use honeycomb structure according to claim 1, the method comprising:
an outer-walled structure preparation process of extruding a material through a die for forming the honeycomb structure having an outer peripheral side wall;
an outer peripheral section processing process of removing at least a portion of the outer peripheral side wall of the honeycomb structure to form the through-hole groove and the through-hole inlet in the outer peripheral section; and
a crushing process of crushing the honeycomb structure formed with the through-hole groove and the through-hole inlet into a size of $10^{-12}$ m$^3$ or larger and smaller than $10^{-8}$ m$^3$.

13. A method for producing a medical use honeycomb structure according to claim 1, the medical use honeycomb structure comprising carbonate apatite in composition, the method comprising:

an outer-walled structure preparation process of extruding a mixture of calcium hydroxide mixed with an organic binder through a die for forming the honeycomb structure having an outer peripheral side wall;
a debindering process of debindering the honeycomb structure;
a carbonation process of performing a carbonation treatment of the honeycomb structure simultaneously with or subsequently to the debindering process; and
an apatite preparation process of adding an aqueous phosphate solution to the honeycomb structure that has undergone the carbonation process, wherein
the method further comprises, at any stage after the outer-walled structure preparation process, an outer peripheral section processing process of removing at least a portion of the outer peripheral side wall of the honeycomb structure to form the through-hole groove among a plurality of through-hole grooves and the through-hole inlet in the outer peripheral section.

14. A method for producing the medical use honeycomb structure according to claim 1, the medical use honeycomb structure comprising carbonate apatite in composition, the method comprising:
an outer-walled structure preparation process of extruding a mixture of calcium sulfate mixed with an organic binder through a die for forming the honeycomb structure having an outer peripheral side wall;
a debindering process of debindering the honeycomb structure; and
an apatite preparation process of adding an aqueous solution containing a carbonate and a phosphate or sequentially adding an aqueous solution containing a carbonate and an aqueous solution containing a phosphate to the honeycomb structure that has undergone the debindering process, wherein
the method comprises, at any stage after the outer-walled structure preparation process, an outer peripheral section processing process of removing at least a portion of the outer peripheral side wall of the honeycomb structure to form the through-hole groove among a plurality of through-hole grooves and the trough-hole inlet among a plurality of through-hole inlets in the outer peripheral section.

15. A medical use honeycomb structure, comprising:
a plurality of through-holes extending in one direction, wherein
an outer peripheral section of the medical use honeycomb structure has a through-hole groove formed by scraping a side wall of a through-hole among the plurality of through-holes,
and a through-hole inlet among a plurality of through-hole inlets, wherein the through-hole inlet is adjacent to the through-hole groove,
wherein a ratio of the number of the plurality of through-hole inlets to the number of the plurality of through-holes in an outermost layer is 0.05 or more.

16. The medical use honeycomb structure according to claim 15, wherein a ratio of a length in a longitudinal direction to a length in a width direction of the through-hole groove is 1.5 or more.

17. The medical use honeycomb structure according to claim 15, wherein at least an outermost layer and a second outer layer in an inner side thereof are each provided with a respective through-hole groove and a respective through-hole inlet.

18. The medical use honeycomb structure according to claim 15, wherein a piercing hole which pierces the side wall of the through-hole is provided.

19. The medical use honeycomb structure according to claim 15, wherein a thickness of an outer peripheral side wall of the outer peripheral section is 300 µm or smaller.

20. The medical use honeycomb structure according to claim 15, wherein a ratio of a length in a longitudinal direction to a diameter of the through-hole is 3 or more.

21. The medical use honeycomb structure according to claim 15, wherein the medical use honeycomb structure is made of a composition containing at least one type selected from the group consisting of apatite, $\beta$-tricalcium phosphate, $\alpha$-tricalcium phosphate and octacalcium phosphate.

22. The medical use honeycomb structure according to claim 15, wherein the medical use honeycomb structure is made of a composition containing carbonate apatite.

23. A crushed product of a medical use honeycomb structure according to claim 15.

24. The crushed product according to claim 23, wherein the crushed product has a size of $10^{-12}$ m$^3$ or larger and smaller than $10^{-8}$ m$^3$.

25. A method for producing the medical use honeycomb structure according to claim 15, the method comprising:
    an outer-walled structure preparation process of extruding a material through a die for forming the honeycomb structure having an outer peripheral side wall; and
    an outer peripheral section processing process of removing at least a portion of the outer peripheral side wall of the honeycomb structure to form the through-hole groove and the through-hole inlet in the outer peripheral section.

26. A method for producing a medical use honeycomb structure crushed product from the medical use honeycomb structure according to claim 15, the method comprising:
    an outer-walled structure preparation process of extruding a material through a die for forming the honeycomb structure having an outer peripheral side wall;
    an outer peripheral section processing process of removing at least a portion of the outer peripheral side wall of the honeycomb structure to form the through-hole groove and the through-hole inlet in the outer peripheral section; and
    a crushing process of crushing the honeycomb structure formed with the through-hole groove and the through-hole inlet into a size of $10^{-12}$ m$^3$ or larger and smaller than $10^{-8}$ m$^3$.

27. A method for producing a medical use honeycomb structure according to claim 15, the medical use honeycomb structure comprising carbonate apatite in composition, the method comprising:
    an outer-walled structure preparation process of extruding a mixture of calcium hydroxide mixed with an organic binder through a die for forming the honeycomb structure having an outer peripheral side wall;
    a debindering process of debindering the honeycomb structure;
    a carbonation process of performing a carbonation treatment of the honeycomb structure simultaneously with or subsequently to the debindering process; and
    an apatite preparation process of adding an aqueous phosphate solution to the honeycomb structure that has undergone the carbonation process, wherein
    the method further comprises, at any stage after the outer-walled structure preparation process, an outer peripheral section processing process of removing at least a portion of the outer peripheral side wall of the honeycomb structure to form the through-hole groove among a plurality of through-hole grooves and the through-hole inlet in the outer peripheral section.

28. A method for producing the medical use honeycomb structure according to claim 15, the medical use honeycomb structure comprising carbonate apatite in composition, the method comprising:
    an outer-walled structure preparation process of extruding a mixture of calcium sulfate mixed with an organic binder through a die for forming the honeycomb structure having an outer peripheral side wall;
    a debindering process of debindering the honeycomb structure; and
    an apatite preparation process of adding an aqueous solution containing a carbonate and a phosphate or sequentially adding an aqueous solution containing a carbonate and an aqueous solution containing a phosphate to the honeycomb structure that has undergone the debindering process, wherein
    the method comprises, at any stage after the outer-walled structure preparation process, an outer peripheral section processing process of removing at least a portion of the outer peripheral side wall of the honeycomb structure to form the through-hole groove among a plurality of through-hole grooves and the plurality of trough-hole inlets in the outer peripheral section.

* * * * *